United States Patent
Su et al.

(10) Patent No.: US 7,238,477 B2
(45) Date of Patent: *Jul. 3, 2007

(54) METHODS TO INCREASE NUCLEOTIDE SIGNALS BY RAMAN SCATTERING

(75) Inventors: Xing Su, Cupertino, CA (US); Andrew A. Berlin, San Jose, CA (US); Selena Chan, San Jose, CA (US); Steven J. Kirch, Pleasanton, CA (US); Tac-Woong Koo, South San Francisco, CA (US); Gabi Neubauer, Los Gatos, CA (US); Valluri Rao, Saratoga, CA (US); Narayanan Sundararajan, San Francisco, CA (US); Mineo Yamakawa, Campbell, CA (US)

(73) Assignee: Intel Corporation, Santa Clara, CA (US)

( * ) Notice: Subject to any disclaimer, the term of this patent is extended or adjusted under 35 U.S.C. 154(b) by 465 days.

This patent is subject to a terminal disclaimer.

(21) Appl. No.: 10/660,902

(22) Filed: Sep. 12, 2003

(65) Prior Publication Data

US 2004/0126790 A1    Jul. 1, 2004

Related U.S. Application Data

(63) Continuation-in-part of application No. 10/099,287, filed on Mar. 14, 2002, now Pat. No. 6,972,173, and a continuation-in-part of application No. 09/962,555, filed on Sep. 24, 2001, now Pat. No. 6,982,165.

(51) Int. Cl.
| | |
|---|---|
| C12Q 1/68 | (2006.01) |
| C12P 19/34 | (2006.01) |
| C07H 21/02 | (2006.01) |
| G01N 21/63 | (2006.01) |

(52) U.S. Cl. .................. 435/6; 435/91.2; 536/23.1; 536/24.3; 422/82.06

(58) Field of Classification Search ............... None
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,962,037 A | 10/1990 | Jett et al. | |
| 5,038,853 A | 8/1991 | Callaway | |
| 5,306,403 A * | 4/1994 | Vo-Dinh | 204/450 |
| 5,401,511 A | 3/1995 | Margalit | |
| 5,405,747 A | 4/1995 | Jett et al. | |
| 5,610,287 A | 3/1997 | Nikiforov | |
| 5,674,743 A | 10/1997 | Ulmer | |
| 5,707,804 A | 1/1998 | Mathies et al. | |
| 5,721,102 A | 2/1998 | Vo-Dinh | |
| 5,776,674 A | 7/1998 | Ulmer | |
| 5,783,389 A | 7/1998 | Vo-Dinh | |
| 5,814,516 A | 9/1998 | Vo-Dinh | |
| 5,866,336 A | 2/1999 | Nazarenko et al. | |
| 5,867,266 A | 2/1999 | Craighead | |
| 5,904,824 A | 5/1999 | Oh | |
| 5,919,622 A | 7/1999 | Macho | |
| 5,942,609 A * | 8/1999 | Hunkapiller et al. | 536/25.3 |
| 5,986,076 A | 11/1999 | Rothschild | |
| 6,002,471 A | 12/1999 | Quake | |
| 6,033,546 A | 3/2000 | Ramsey | |
| 6,040,191 A | 3/2000 | Grow | |
| 6,054,495 A | 4/2000 | Markowitz | |
| 6,090,589 A | 7/2000 | Dimond | |
| 6,127,120 A | 10/2000 | Graham et al. | |
| 6,136,543 A | 10/2000 | Anazawa et al. | |
| 6,140,053 A | 10/2000 | Koster | |
| 6,149,868 A | 11/2000 | Natan et al. | |
| 6,174,677 B1 | 1/2001 | Vo-Dinh | |
| 6,180,372 B1 | 1/2001 | Franzen | |
| 6,180,415 B1 | 1/2001 | Schultz et al. | |

(Continued)

FOREIGN PATENT DOCUMENTS

WO    WO 9944045 A1 *   9/1999

(Continued)

OTHER PUBLICATIONS

Sauer et al. (Apr. 2001) Single molecule DNA sequencing in submicrometer channels: state of the art and future prospects. Journal of Biotechnology, vol. 86: 181-201.*

(Continued)

Primary Examiner—Jeffrey Fredman
Assistant Examiner—Angela Bertagna
(74) Attorney, Agent, or Firm—Darby & Darby

(57) ABSTRACT

The methods and apparatus disclosed herein concern nucleic acid sequencing by enhanced Raman spectroscopy. In certain embodiments of the invention, nucleotides are covalently attached to Raman labels before incorporation into a nucleic acid. In other embodiments, unlabeled nucleic acids are used. Exonuclease treatment of the nucleic acid results in the release of labeled or unlabeled nucleotides that are detected by Raman spectroscopy. In alternative embodiments of the invention, nucleotides released from a nucleic acid by exonuclease treatment are covalently cross-linked to nanoparticles and detected by surface enhanced Raman spectroscopy (SERS), surface enhanced resonance Raman spectroscopy (SERRS) and/or coherent anti-Stokes Raman spectroscopy (CARS). Other embodiments of the invention concern apparatus for nucleic acid sequencing.

12 Claims, 11 Drawing Sheets

U.S. PATENT DOCUMENTS

| | | | |
|---|---|---|---|
| 6,210,896 B1 | 4/2001 | Chan | |
| 6,214,246 B1 | 4/2001 | Craighead | |
| 6,219,137 B1 | 4/2001 | Vo-Dinh | |
| 6,225,068 B1 | 5/2001 | Wolfrum | |
| 6,313,914 B1 | 11/2001 | Roe | |
| 6,344,272 B1 | 2/2002 | Oldenburg et al. | |
| 6,376,177 B1 | 4/2002 | Poponin | |
| 6,878,539 B1* | 4/2005 | Fritzsche et al. | 435/287.2 |
| 2002/0058273 A1 | 5/2002 | Shipwash | |
| 2002/0102595 A1 | 8/2002 | Davis | |
| 2003/0058799 A1 | 3/2003 | Yamakawa et al. | |
| 2003/0059820 A1 | 3/2003 | Vo-Dinh | |

FOREIGN PATENT DOCUMENTS

| | | |
|---|---|---|
| WO | WO 03/027307 A2 | 4/2003 |
| WO | WO 03/078649 A2 | 9/2003 |

OTHER PUBLICATIONS

Matsuura et al. (Aug. 15, 2001) Real-time observation of a single DNA digestion by lambda exonuclease under a fluorescence microscope field. Nucleic Acids Reasearch. vol. 29: e79.*

Molecular Probes product information, Thiol reactive Probes, MP00003, Jul. 8, 2003.*

Nanogold Labeling Reagents, Http://www.Nanoprobes.com/Labrgts.html (accessed Feb. 15, 2006).*

Vo-Dinh Surfce-enhanced Raman spectroscopy using metallic nanostructures. Trends in Analytical Chemistry (1998) 17: 557-582.*

Elghanian et al. Selective colorimetric detection of polynucleotides based on the distance-dependent optical properties of gold nanoparticles. Science (1997) 277: 1078-1081.*

Chen et al. The metal cation effect on the SERS of interfacial D2O and H2O. Chemical Physics Letters (1984) 108(1): 32-38.*

Ambrose et al., "Application of Single Molecule Detection to DNA Sequencing and Sizing", Ber. Bunsenges. Phys. Chem., vol. 97, No. 12, pp. 1535-1542, 1993.

Dörre et al., "Techniques for single molecule sequencing", Bioimaging, vol. 5, No. 3, pp. 139-152, 1997.

Goodwin et al., "Progress toward DNA sequencing at a single molecular level", Experimental Technique of Physics, vol. 41, No. 2, pp. 279-294, 1995.

Goodwin et al., "Single-Molecule Detection in Liquids by Laser-Induced Fluorescence", Accounts of Chemical Research, vol. 29, pp. 607-613, 1996.

Goodwin et al., "Application of Single Molecule Detection to DNA Sequencing", Nucleosides & Nucleotides, vol. 16, No. 5/6, pp. 543-550, 1997.

Kneipp et al., "Detection and identification of a single DNA base molecule using surface-enhance Raman scattering (SERS)", Physical Review E. Statistical Physics, Plasmas, Fluids, and Related Interdisciplinary Topics, American Institute of Physics, vol. 47, No. 6, pp. R6281-R6284, 1998.

Schecker et al., "Flow-Based Continuous DNA Sequencing via Single Molecule Detection of Enzymatically cleaved Fluorescent Nucleotides", SPIE, vol. 2386, pp. 4-12, 1995.

Uibel et al., "Fiber-Optic Raman Spectroscopy for in Situ Monitoring of Metal-Ion Complexation by Ligands Immobilized onto Silica Gel", Applied Spectroscopy, vol. 54, No. 12, pp. 1868-1875, 2000.

Machara, N. et al. (1998). Efficient Detection of Single Molecules Eluting Off an Optically Trapped Microsphere, Bioimaging, 6:33-42.

1997 DOE Human Genome Program Contractor-Grantee Workshop VI, located at <http://www.ornl.gov/hgmis/publicat/97santa/seqtech.html. (2 pages).

M. Sauer, "New Strategies for DNA Sequencing Using Diode Laser-Based Time-Resolved Fluorescence Detection," located at <http:// pc-cube01.pci.uni-heidelberg.de/alt/msauer/emsproject01.htm.>Visited on Nov. 12, 2001. (2 pages).

Lee and Meisel (1982)., J. Phys. Chem. 86:3391-3395.

Feldheim (2001). "Assembly of Metal Nanoparticle Arrays Using Molecular Bridges," The Electrochemical Society Interface, 22-25.

B. Dubertret et al. (2001). "Single-Mismatch Detection Using Gold-Quenched Fluorescent Oligonucelotides," Nature Biotechnology, 19:365-370.

Bloch et al. (2001). "Optics with an atom laser beam," Phys. Rev. Lett. 87.

Ivanisevic et al. (2001). "Dip-Pen Nanolithography on Semiconductor Surfaces," J. Am. Chem. Soc., 123: 7887-7889.

Siegel (1987). "Ion Beam Lithography," VLSI Electronics, Microstructure Science, 16.

Jin et al. (2001). "Photoinduced Conversion of Silver Nanospheres to Nanoprisms," Science, 294: 1901-1903.

Castro, A. et al. (1993). "Fluorescence Detection and Sizing Measurement of Single DNA Molecules," Analytical Chemistry, American Chemical Society, 65(7):849-852.

Szoelloesi, J. et al. (1998). "Application of Fluorescence Resonance Energy Transfer in the Clinical Laboratory: Routine and Research," Cytometry, 34(4): 159-179.

Watson, N. et al. (1998). "Detection of DNA Sequence by Surface Enhanced Resonance Raman Scattering of a Modified DNA Probe," Progress in Forensic Genetics, 7(1167):6-8.

Weiss, (1998). "Fluorescence Spectyroscopy of Single Biomolecules" Science, 283(5408):1676-1683.

Berger & Kimmel, Guide to Molecular Cloning Techniques Academic Press, New York, NY. 1987.

Sambrook, et al, Molecular Cloning: A Laboratory Manual 2$^{nd}$ Ed. Cold Spring Harbor Press, Cold Spring Harbor, NY. 1989.

Holmstrom et al. (1993). "A Highly Sensitive and Fast Nonradioactive Method for Detection of Polymerase Chain Reaction Products," Analytical Biochemistry 209:278-283.

Running et al. (1990)"A Procedure for Productive Coupling of Synthetic Oligonucleotides to Polystyrene Microtiter Wells for Hybridization Capture," Bio Techniques 8:276-277.

Newton et al.(1993). "The Production of PCR Products with 5' Single-Stranded Tails Using Primers That Incorporate Novel Phosphoramidite Intermediates," Nucleic Acids Res. 21:1155-1162.

Goodman and Tippin. (2000). "The Expanding Polymerase Universe," Nature Reviews: Molecular Cell Biology 1:101-109.

Craighead (2000). "Nanoelectrical Systems," Science 290:1532-1536.

Woolley and Mathies. (1994). "Ultra-high-speed DNA fragment separations using microfabricated capillary array electrophoresis chips," PNAS 91:11348-11352.

Effenhauser et al. (1994). "High-Speed Separation of Antisense Oligonucleotides on a Micromachined Capillary Electrophoresis Device," Analytical Chemistry 66:2949-2953.

Harrison et al. (1993), "Micromachining a Miniaturized Capillary Electrophoresis-Based Chemical Analysis System on a Chip," Science 261:895-897.

Rasmussen et al. (1991). "Covalent Immobilization of DNA onto Polystyrene Microwells: The Molecules Are Only Bound at the 5'End," Anal. Biochem. 198:138-142.

Anderson et al. "Fabrication of Topologically Complex Three-Dimensional Microfluidic Systems in PDMS by Rapid Prototyping," Anal. Chem. 72:3158-3164, 2000.

Townsend and Tipson, eds. (1978). Nucleic Acid Chemistry: Improved and new synthetic Procedures, Methods, and Techniques, Part One. John Wiley & Sons, Inc.: New York City, NY, pp. v-xv Table of Contents.

Walker et al. (1999). "Mechanical Manipulation of Bone and Cartilage cells With 'Optical Tweezers', " FEBS Lett. 459:39-42.

Bennik et al. (1999). "Single-Molecule manipulation of Double-Stranded DNA Using Optical Tweezers: Interaction Studies of DNA with RecA and YOYO-1," Cytometry 36:200-208.

Mehta et al. (1999). "Single-Molecule Biomechanics with Optical Methods," Science 283:1689-1695.

Smith et al. (1999). "Inexpensive Optical Tweezers for Undergraduate Laboratories," Am. J. Phys. 67:26-35.

* cited by examiner

METHODS TO INCREASE NUCLEOTIDE SIGNALS BY RAMAN SCATTERING

RELATED APPLICATIONS

The present application is a continuation-in-part of U.S. patent application Ser. No. 10/099,287, filed on Mar. 14, 2002, issued as U.S. Pat. No. 6,972,173 on Dec. 6, 2005; and a continuation-in-part of U.S. patent application Ser. No. 09/962,555, filed Sep. 24, 2001, issued as U.S. Pat. No. 6,982,165 on Jan. 3, 2006.

FIELD OF THE INVENTION

The present methods and apparatus relate to the fields of molecular biology and genomics. More particularly, the methods and apparatus concern nucleic acid sequencing.

BACKGROUND

Genetic information is stored in the form of very long molecules of deoxyribonucleic acid (DNA), organized into chromosomes. The human genome contains approximately three billion bases of DNA sequence. This DNA sequence information determines multiple characteristics of each individual. Many common diseases are based at least in part on variations in DNA sequence.

Determination of the entire sequence of the human genome has provided a foundation for identifying the genetic basis of such diseases. However, a great deal of work remains to be done to identify the genetic variations associated with each disease. That would require DNA sequencing of portions of chromosomes in individuals or families exhibiting each such disease, in order to identify specific changes in DNA sequence that promote the disease. Ribonucleic acid (RNA), an intermediary molecule in processing genetic information, may also be sequenced to identify the genetic bases of various diseases.

Existing methods for nucleic acid sequencing, based on detection of fluorescently labeled nucleic acids that have been separated by size, are limited by the length of the nucleic acid that can be sequenced. Typically, only 500 to 1,000 bases of nucleic acid sequence can be determined at one time. This is much shorter than the length of the functional unit of DNA, referred to as a gene, which can be tens or even hundreds of thousands of bases in length. Using current methods, determination of a complete gene sequence requires that many copies of the gene be produced, cut into overlapping fragments and sequenced, after which the overlapping DNA sequences may be assembled into the complete gene. This process is laborious, expensive, inefficient and time-consuming. It also typically requires the use of fluorescent or radioactive labels, which can potentially pose safety and waste disposal problems.

More recently, methods for nucleic acid sequencing have been developed involving hybridization to short oligonucleotides of defined sequenced, attached to specific locations on DNA chips. Such methods may be used to infer short nucleic acid sequences or to detect the presence of a specific nucleic acid in a sample, but are not suited for identifying long nucleic acid sequences.

BRIEF DESCRIPTION OF THE DRAWINGS

The following drawings form part of the present specification and are included to further demonstrate certain aspects of the disclosed embodiments of the invention. The embodiments of the invention may be better understood by reference to one or more of these drawings in combination with the detailed description of specific embodiments of the invention presented herein.

DESCRIPTION OF ILLUSTRATIVE EMBODIMENTS

Figure 1:
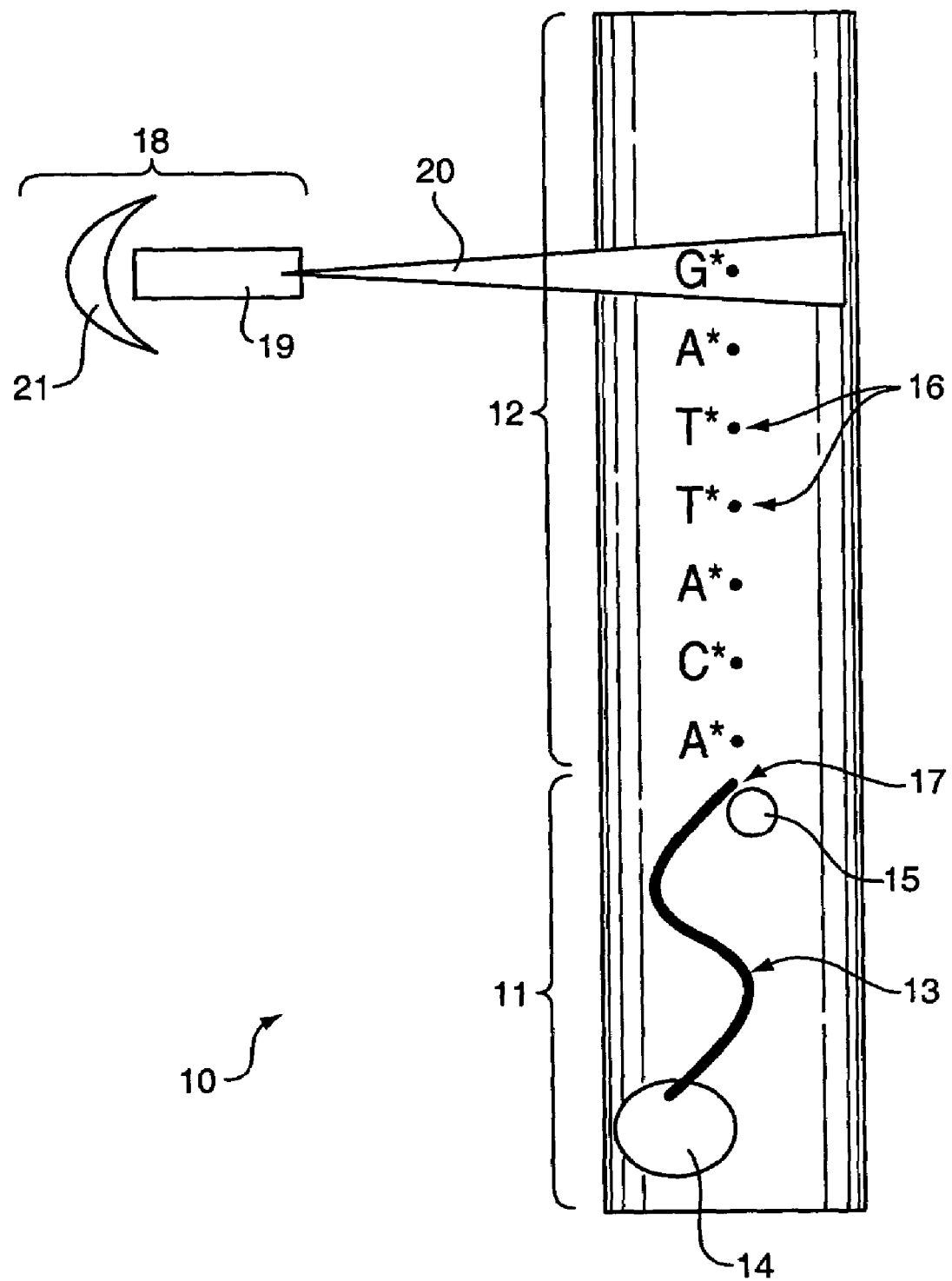
FIG. 1 illustrates an exemplary apparatus 10 (not to scale) and method for nucleic acid 13 sequencing, using nucleotides 16 covalently attached to Raman labels.

The disclosed methods and apparatus are of use for the rapid, automated sequencing of nucleic acids. In particular embodiments of the invention, the methods and apparatus are suitable for obtaining the sequences of very long nucleic acid molecules of greater than 1,000, greater than 2,000, greater than 5,000, greater than 10,000 greater than 20,000, greater than 50,000, greater than 100,000 or even more bases in length. Advantages over prior art methods include the ability to read long nucleic acid sequences in a single sequencing run, greater speed of obtaining sequence data, decreased cost of sequencing and greater efficiency in operator time required per unit of sequence data.

In various embodiments of the invention, sequence information may be obtained during the course of a single sequencing run, using a single nucleic acid molecule. In other embodiments of the invention, multiple copies of a nucleic acid molecule may be sequenced in parallel or sequentially to confirm the nucleic acid sequence or to obtain complete sequence data. In alternative embodiments of the invention, both the nucleic acid molecule and its complementary strand may be sequenced to confirm the accuracy of the sequence information. In various embodiments, a nucleic acid to be sequenced may be attached, either covalently or non-covalently to a surface. In particular embodiments, nucleotides may be released from a surface-attached nucleic acid, for example by exonuclease treatment. Released nucleotides may be transported, for example, through a microfluidic system to a Raman detector, to allow detection of released nucleotides without background Raman signals from the nucleic acid, exonuclease and/or other components of the system.

In certain embodiments of the invention, the nucleic acid to be sequenced is DNA, although it is contemplated that other nucleic acids comprising RNA or synthetic nucleotide analogs could be sequenced as well. The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

In various embodiments of the invention, unlabeled nucleotides may be detected by Raman spectroscopy, for example by surface enhanced Raman spectroscopy (SERS), surface enhanced resonance Raman spectroscopy (SERRS), coherent anti-Stokes Raman spectroscopy (CARS) or other known Raman detection techniques. In alternative embodiments, nucleotides may be covalently attached to Raman labels to enhance the Raman signal. In some embodiments, labeled nucleotides may be incorporated into a newly synthesized nucleic acid strand using standard nucleic acid polymerization techniques. Typically, either a primer of specific sequence or one or more random primers is allowed to hybridize to a template nucleic acid. Upon addition of a polymerase and labeled nucleotides, the Raman labeled nucleotides are covalently attached to the 3' end of the primer, resulting in the formation of a labeled nucleic acid strand complementary in sequence to the template. The labeled strand may be separated from the unlabeled template, for example by heating to about 95° C. or other known methods. The two strands may be separated from each other by techniques well known in the art. For example, the primer oligonucleotide may be covalently modified with a biotin residue and the resulting biotinylated nucleic acid may be separated by binding to an avidin or streptavidin coated surface.

In alternative embodiments of the invention, either labeled or unlabeled single-stranded nucleic acid molecules may be digested with one or more exonucleases. The skilled artisan will realize that the disclosed methods are not limited to exonucleases per se, but may utilize any enzyme or other reagent capable of sequentially removing nucleotides from at least one end of a nucleic acid. In certain embodiments of the invention, labeled or unlabeled nucleotides are sequentially released from the 3' end of the nucleic acid. After separation from the nucleic acid, the nucleotides are detected by a Raman detection unit. Information on sequentially detected nucleotides is used to compile a sequence of the nucleic acid. Nucleotides released from the 3' end of a nucleic acid may be transported down a microfluidic flow path past a Raman detector. In particular embodiments, the detector is capable of detecting labeled or unlabeled nucleotides at the single molecule level. The order of detection of the nucleotides by the Raman detector is the same as the order in which the nucleotides are released from the 3' end of the nucleic acid. The sequence of the nucleic acid can thus be determined by the order in which released nucleotides are detected. Where a complementary strand is sequenced, the template strand will be complementary in sequence according to standard Watson-Crick hydrogen bond base-pairing (i.e., A-T and G-C or A-U and G-C, depending on whether DNA or RNA is sequenced).

In certain alternative embodiments, a tag molecule may be added to a reaction chamber or flow path upstream of the detection unit. The tag molecule binds to and tags free nucleotides as they are released from the nucleic acid molecule. This post-release tagging avoids problems that are encountered when the nucleotides of the nucleic acid molecule are tagged before their release into solution. For example, the use of bulky Raman label molecules may provide steric hindrance when each nucleotide incorporated into a nucleic acid molecule is labeled before exonuclease treatment, reducing the efficiency and increasing the time required for the sequencing reaction.

In certain embodiments of the invention, each of the four types of nucleotide may be attached to a distinguishable Raman label. In other embodiments of the invention, only the purine nucleotides (cytosine and/or thymine and/or uracil) may be labeled. In one exemplary embodiment, the labeled nucleotides may comprise biotin-labeled deoxycytidine-5'-triphosphate (biotin-dCTP) and digoxigenin-labeled deoxyuridine-5'-triphosphate (digoxigenin-dUTP). In alternative embodiments, no nucleotides are labeled and the unlabeled nucleotides are identified by Raman spectroscopy.

In specific embodiments of the invention, the Raman signals may be enhanced by covalent attachment of nucleotides to nanoparticles. Nanoparticles may be prepared as discussed below and activated by attachment of highly reactive groups, for example epoxide groups, using known methods. For example, nanoparticles may be coated with 3-glycidoxypropyltrimethoxysilane (GOP). GOP contains a terminal highly reactive epoxide group. The use of highly reactive groups such as epoxides allows for rapid formation of covalent bonds between nanoparticles and nucleotides. In some embodiments, the nucleotides may be released from a nucleic acid by exonuclease activity and then reacted with nanoparticles to allow covalent bond formation. Various methods may be employed to allow sufficient time for covalent bonds to form before the nanoparticle-nucleotide complex. For example, a solution containing released nucleotides and activated nanoparticles may be transported by microfluidic flow down a relatively long flow path, allowing sufficient time for covalent bond formation to occur before the nucleotide-nanoparticle complex passes in front of the Raman detector. Flow rate may be further decreased by use of a fluid of high viscosity, for example a glycerol solution. Methods of microfluidic flow of high viscosity solutions are known in the art.

Alternatively, a cyclic process may be employed, wherein a nanoparticle is first allowed to bind to the 3' end of a nucleic acid. The nanoparticle and attached nucleotide may be released from the 3' end of the nucleic acid by exonuclease activity or chemical treatment. For example, the phosphodiester bond attaching the terminal nucleotide to the nucleic acid may be cleaved by treatment with acid or base. The electron-withdrawing effect of the attached nanoparticle may render the terminal phosphodiester bond particularly labile to cleavage, allowing removal of a single nucleotide at a time. Following release, another nanoparticle may be reacted with the 3' end of the nucleic acid and the process repeated in a cycle. Alternatively, a 3' exonuclease may be used to release the nucleotide-nanoparticle complex. Steric hindrance from the nanoparticle with exonuclease activity may be avoided by using a linker arm to attach the reactive group (e.g., epoxide) to the nanoparticle. Attachment of the nanoparticle before release of the terminal nucleotide would allow ample time for covalent bond formation. In other alternative embodiments of the invention, the rate of exonuclease activity may be adjusted to coordinate the rates of release of nucleotides and their covalent attachment to nanoparticles. For example, a reaction chamber containing a nucleic acid and exonuclease may be temperature controlled to a reduced temperature, of between 0° C. and room temperature. Once an appropriate temperature has been determined, the nucleotides released by exonuclease activity may enter a flow path where they are mixed with reactive nanoparticles at an elevated temperature, between room temperature and 100° C. The elevated temperature would increase the rate of reactivity of nucleotide and nanoparticle. In various embodiments, temperature ranges from about 0° C. to 5° C., 5° C. to 10° C., 10° C. to 15° C., 15° C. to 20° C. or 20° C. to 25° C. may be used to regulate exonuclease activity. In certain embodiments, temperature ranges from about 20° C. to 25° C., 25° C. to 30° C., 30° C. to 35° C., 35° C. to 40° C., 40° C. to 45° C., 45° C. to 50° C., 50° C. to 55° C., 55° C. to 60° C., 60° C. to 65° C., 65° C. to 70° C., 70° C. to 75° C., 75° C. to 80° C. or 80° C. to 95° C. may be used to regulate the rate of covalent bond formation between nanoparticle and nucleotide. It is well within the routine skill in the art to assay reaction rates as a function of temperature and to select appropriate temperature ranges to coordinate the rates of exonuclease activity and nucleotide-nanoparticle cross-linking.

In some embodiments of the invention, the nanoparticles are silver or gold, but other types of nanoparticles known to provide surface enhanced Raman signals are contemplated. The nanoparticles may either be single nanoparticles, aggregates of nanoparticles, or some mixture of single and aggregated nanoparticles. In certain embodiments, a linker compound may be used to attach the nucleotides to the nanoparticles. The linker compound may be between 1 to 100 nanometers (nm), 2 to 90 nm, 3 to 80 nm, 4 to 70 nm, 5 to 60 nm, 10 to 50 nm, 15 to 40 nm or 20 to 30 nm in length. In certain embodiments, the linker compound may be between 1 to 50, 1 to 5, 2 to 10, 10 to 20 nm or about 5 nm in length. In other embodiments, two or more nanoparticles may be attached together using linker compounds.

The nanoparticle-nucleotide complexes may pass through a flow-through cell where they are detected by SERS, SERRS and/or CARS using a Raman detection unit. In some alternative embodiments of the invention, the nucleotides may be unmodified, while in other alternative embodiments the nucleotides may be modified with one or more Raman labels. In certain embodiments, each type of nucleotide may be attached to a distinguishable Raman label. In other embodiments only pyrimidines may be labeled.

Definitions

As used herein, "a" or "an" may mean one or more than one of an item.

As used herein, "operably coupled" means that there is a functional interaction between two or more units. For example, a detector may be "operably coupled" to a flow-through cell if the detector is arranged so that it may detect analytes, such as nucleotides, as they pass through the flow-through cell.

"Nucleic acid" encompasses DNA, RNA, single-stranded, double-stranded or triple stranded and any chemical modifications thereof. Virtually any modification of the nucleic acid is contemplated. As used herein, a single stranded nucleic acid may be denoted by the prefix "ss", a double stranded nucleic acid by the prefix "ds", and a triple stranded nucleic acid by the prefix "ts." A "nucleic acid" may be of almost any length, from 10, 20, 30, 40, 50, 60, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule.

A "nucleoside" is a molecule comprising a purine or pyrimidine base (adenine—"A", cytosine—"C", guanine—"G", thymine—"T" or uracil—"U") or any chemical modification or structural analog thereof, covalently attached to a pentose sugar such as deoxyribose, ribose or derivatives or analogs of pentose sugars.

A "nucleotide" refers to a nucleoside further comprising at least one phosphate group covalently attached to the pentose sugar. In some embodiments of the invention, the nucleotides are ribonucleoside monophosphates or deoxyribonucleoside monophosphates, although it is anticipated that nucleoside diphosphates or triphosphates could be produced and detected. In other embodiments of the invention, nucleosides may be released from the nucleic acid molecule. It is contemplated that various substitutions or modifications may be made in the structure of the nucleotides, so long as they are capable of being incorporated into a nucleic acid by polymerase activity and released by an exonuclease or equivalent reagent. In embodiments of the invention involving one or more labels attached to one or more types of nucleotide, the label may be attached to any portion of the nucleotide, such as the base, the sugar or the phosphate groups or their analogs. The terms "nucleotide" and "labeled nucleotide" encompass, but are not limited to, all non-naturally nucleotide complexes, such as nucleotide-nanoparticle complexes and nucleotide-label complexes.

A "Raman label" may be any organic or inorganic molecule, atom, complex or structure capable of producing a detectable Raman signal, including but not limited to synthetic molecules, dyes, naturally occurring pigments such as phycoerythrin, organic nanostructures such as $C_{60}$, buckyballs and carbon nanotubes, metal nanostructures such as gold or silver nanoparticles or nanoprisms and nano-scale semiconductors such as quantum dots. Numerous examples of Raman labels are disclosed below. The skilled artisan will realize that such examples are not limiting, and that "Raman label" encompasses any organic or inorganic atom, molecule, compound or structure known in the art that can be detected by Raman spectroscopy.

Nucleic Acids

Nucleic acid molecules to be sequenced may be prepared by any technique known in the art. In certain embodiments of the invention, the nucleic acids are naturally occurring DNA or RNA molecules. Virtually any naturally occurring nucleic acid may be prepared and sequenced by the disclosed methods including, without limit, chromosomal, mitochondrial and chloroplast DNA and ribosomal, transfer, heterogeneous nuclear and messenger RNA (mRNA). Methods for preparing and isolating various forms of nucleic acids are known. (See, e.g., *Guide to Molecular Cloning Techniques*, eds. Berger and Kimmel, Academic Press, New York, N.Y., 1987; *Molecular Cloning: A Laboratory Manual*, 2nd Ed., eds. Sambrook, Fritsch and Maniatis, Cold Spring Harbor Press, Cold Spring Harbor, N.Y., 1989). The methods disclosed in the cited references are exemplary only and any variation known in the art may be used. In cases where single stranded DNA (ssDNA) is to be sequenced, an ssDNA may be prepared from double stranded DNA (dsDNA) by any known method. Such methods may involve heating dsDNA and allowing the strands to separate, or may alternatively involve preparation of ssDNA from dsDNA by known amplification or replication methods, such as cloning into M13. Any such known method may be used to prepare ssDNA or ssRNA. As discussed above, one of the two strands of double-stranded DNA may be separated, for example, by biotin labeling and attachment to avidin or streptavidin using known techniques.

Although certain embodiments of the invention concern preparation of naturally occurring nucleic acids, virtually any type of nucleic acid that can serve as a substrate for an exonuclease or equivalent reagent could potentially be sequenced. For example, nucleic acids prepared by various amplification techniques, such as polymerase chain reaction (PCR™) amplification, could be sequenced. (See U.S. Pat. Nos. 4,683,195, 4,683,202 and 4,800,159.) Nucleic acids to be sequenced may alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts may be isolated from vector DNA, for example, by excision with appropriate restriction endonucleases, followed by agarose gel electrophoresis. Methods for isolation of insert nucleic acids are well known.

Isolation of Single Nucleic Acid Molecules

In certain embodiments of the invention, the nucleic acid molecule to be sequenced is a single molecule of ssDNA or ssRNA. A variety of methods for selection and manipulation of single nucleic acid molecules may be used, for example, hydrodynamic focusing, micro-manipulator coupling, optical trapping, or a combination of these and similar methods. (See, e.g., Goodwin et al., 1996, Acc. Chem. Res. 29:607–619; U.S. Pat. Nos. 4,962,037; 5,405,747; 5,776, 674; 6,136,543; 6,225,068.)

In certain embodiments of the invention, microfluidics or nanofluidics may be used to sort and isolate nucleic acid molecules. Hydrodynamics may be used to manipulate the movement of nucleic acids into a microchannel, microcapillary, or a micropore. In one embodiment of the invention, hydrodynamic forces may be used to move nucleic acid molecules across a comb structure to separate single nucleic acid molecules. Once the nucleic acid molecules have been separated, hydrodynamic focusing may be used to position the molecules within a reaction chamber. A thermal or electric potential, pressure or vacuum can also be used to provide a motive force for manipulation of nucleic acids. In exemplary embodiments of the invention, manipulation of nucleic acids for sequencing may involve the use of a channel block design incorporating microfabricated channels and an integrated gel material (see U.S. Pat. Nos. 5,867,266 and 6,214,246).

In another embodiment of the invention, a sample containing the nucleic acid molecule may be diluted prior to coupling to an immobilization surface. In exemplary embodiments of the invention, the immobilization surface may be in the form of magnetic or non-magnetic beads or other discrete structural units. At an appropriate dilution, each bead will have a statistical probability of binding zero or one nucleic acid molecule. Beads with one attached nucleic acid molecule may be identified using, for example, fluorescent dyes and flow cytometer sorting or magnetic sorting. Depending on the relative sizes and uniformity of the beads and the nucleic acids, it may be possible to use a magnetic filter and mass separation to separate beads containing a single bound nucleic acid molecule. In other embodiments of the invention, multiple nucleic acids attached to a single bead or other immobilization surface may be sequenced.

In alternative embodiments of the invention, a coated fiber tip may be used to generate single molecule nucleic acids for sequencing (e.g., U.S. Pat. No. 6,225,068). In other alternative embodiments, the immobilization surfaces may be prepared to contain a single molecule of avidin or other cross-linking agent. Such a surface could attach a single biotinylated nucleic acid molecule to be sequenced. This embodiment is not limited to the avidin-biotin binding system, but may be adapted to any known coupling system.

In other alternative embodiments of the invention, an optical trap may be used for manipulation of single molecule nucleic acid molecules for sequencing. (E.g., U.S. Pat. No. 5,776,674). Exemplary optical trapping systems are commercially available from Cell Robotics, Inc. (Albuquerque, N. Mex.), S+L GmbH (Heidelberg, Germany) and P.A.L.M. Gmbh (Wolfratshausen, Germany).

Raman Labels

Certain embodiments of the invention may involve attaching a label to the nucleotides to facilitate their measurement by the detection unit. Non-limiting examples of labels that could be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins and aminoacridine. These and other Raman labels may be obtained from commercial sources (e.g., Molecular Probes, Eugene, Oreg.).

Polycyclic aromatic compounds may function as Raman labels, as is known in the art. Other labels that may be of use for particular embodiments of the invention include cyanide, thiol, chlorine, bromine, methyl, phosphorus and sulfur. In certain embodiments of the invention, carbon nanotubes may be of use as Raman labels. The use of labels in Raman spectroscopy is known (e.g., U.S. Pat. Nos. 5,306,403 and 6,174,677). The skilled artisan will realize that the Raman labels used should generate distinguishable Raman spectra and may be specifically bound to or associated with different types of nucleotides.

Labels may be attached directly to the nucleotides or may be attached via various linker compounds. Cross-linking reagents and linker compounds of use in the disclosed methods are further described below. Alternatively, nucleotides that are covalently attached to Raman labels are available from standard commercial sources (e.g., Roche Molecular Biochemicals, Indianapolis, Ind.; Promega Corp., Madison, Wis.; Ambion, Inc., Austin, Tex.; Amersham Pharmacia Biotech, Piscataway, N.J.). Raman labels that contain reactive groups designed to covalently react with other molecules, such as nucleotides, are commercially available (e.g., Molecular Probes, Eugene, Oreg.). Methods for preparing labeled nucleotides and incorporating them into nucleic acids are known (e.g., U.S. Pat. Nos. 4,962,037; 5,405,747; 6,136,543; 6,210,896).

Nanoparticles

Certain embodiments of the invention involve the use of nanoparticles to enhance the Raman signal obtained from nucleotides. In some embodiments of the invention, the nanoparticles are silver or gold nanoparticles, although any nanoparticles capable of providing a surface enhanced Raman spectroscopy (SERS) signal may be used. In alternative embodiments of the invention, the nanoparticles may be nanoprisms (Jin et al., Science 294:1902–3, 2001.) In various embodiments of the invention, nanoparticles of between 1 nm and 2 micrometers (μm) in diameter may be used. In alternative embodiments of the invention, nanoparticles of between 2 nm to 1 μm, 5 nm to 500 nm, 5 nm to 200 nm, 10 nm to 200 nm, 20 nm to 100 nm, 30 nm to 80 nm, 40 nm to 70 nm or 50 to 60 nm diameter are contemplated. In certain embodiments of the invention, nanoparticles with an average diameter of 10 to 50 nm, 50 to 100 nm or about 100 nm are contemplated. The nanoparticles may be approximately spherical, rod-like, edgy, faceted or pointy in shape, although nanoparticles of any shape or of irregular shape may be used. Methods of preparing nanoparticles are known (e.g., U.S. Pat. Nos. 6,054,495; 6,127,120; 6,149,868; Lee and Meisel, *J. Phys. Chem.* 86:3391–3395, 1982; Jin et al., 2001). Nanoparticles may also be obtained from commercial sources (e.g., Nanoprobes Inc., Yaphank, N.Y.; Polysciences, Inc., Warrington, Pa.).

In certain embodiments of the invention, the nanoparticles may be single nanoparticles and/or random aggregates of nanoparticles (colloidal nanoparticles). In other embodiments of the invention, nanoparticles may be cross-linked to produce particular aggregates of nanoparticles, such as dimers, trimers, tetramers or other aggregates. Certain alternative embodiments may use heterogeneous mixtures of aggregates of different size, while other alternative embodiments may use homogenous populations of nanoparticles. In certain embodiments, aggregates containing a selected number of nanoparticles (dimers, trimers, etc.) may be enriched or purified by known techniques, such as ultracentrifugation in sucrose solutions. In various embodiments of the invention, nanoparticle aggregates of about 100, 200, 300, 400, 500, 600, 700, 800, 900 to 1000 nm in size or larger are contemplated.

Methods of cross-linking nanoparticles are known (e.g., Feldheim, "Assembly of metal nanoparticle arrays using molecular bridges," The Electrochemical Society Interface, Fall, 2001, pp. 22–25). Gold nanoparticles may be cross-linked, for example, using bifunctional linker compounds bearing terminal thiol or sulfhydryl groups. Upon reaction with gold nanoparticles, the linker forms nanoparticle dimers that are separated by the length of the linker. In other embodiments of the invention, linkers with three, four or more thiol groups may be used to simultaneously attach to multiple nanoparticles (Feldheim, 2001). The use of an excess of nanoparticles to linker compounds prevents formation of multiple cross-links and nanoparticle precipitation. Aggregates of silver nanoparticles may be formed by standard synthesis methods known in the art.

In alternative embodiments of the invention, the nanoparticles may be modified to contain various reactive groups before they are attached to linker compounds. Modified nanoparticles are commercially available, such as Nanogold® nanoparticles from Nanoprobes, Inc. (Yaphank, N.Y.). Nanogold® nanoparticles may be obtained with either single or multiple maleimide, amine or other groups attached per nanoparticle. The Nanogold® nanoparticles are also available in either positively or negatively charged form. Such modified nanoparticles may be attached to a variety of known linker compounds to provide dimers, trimers or other aggregates of nanoparticles.

The type of linker compound used is not limiting, so long as it results in the production of small aggregates of nanoparticles that will not precipitate in solution. In some embodiments of the invention, the linker group may comprise phenylacetylene polymers (Feldheim, 2001). Alternatively, linker groups may comprise polytetrafluoroethylene, polyvinyl pyrrolidone, polystyrene, polypropylene, polyacrylamide, polyethylene or other known polymers. The linker compounds of use are not limited to polymers, but may also include other types of molecules such as silanes, alkanes, derivatized silanes or derivatized alkanes.

In various embodiments of the invention, the nanoparticles may be covalently attached to nucleotides. In alternative embodiments of the invention, the nucleotides may be directly attached to the nanoparticles, or may be attached to linker compounds that are covalently or non-covalently bonded to the nanoparticles. In such embodiments of the invention, rather than cross-linking two or more nanoparticles together the linker compounds may be used to attach a nucleotide to a nanoparticle or a nanoparticle aggregate. In particular embodiments of the invention, the nanoparticles may be coated with derivatized silanes. Such modified silanes may be covalently attached to nucleotides using standard methods. Various methods known for cross-linking nucleic acids to surfaces discussed below may also be used to attach nucleotides to nanoparticles. It is contemplated that the linker compounds used to attach nucleotides may be of almost any length, ranging from about 0.05, 0.1, 0.2, 0.5, 0.75, 1, 2, 3, 4, 5, 6, 7, 8, 9, 10, 11, 12, 13, 14, 15, 16, 17, 18, 19, 20, 21, 22, 23, 24, 25, 27, 30, 35, 40, 45, 50, 55, 60, 65, 60, 80, 90 to 100 nm or even greater length. Certain embodiments of the invention may use linkers of heterogeneous length.

In other embodiments of the invention, nucleotides may be adsorbed on the surface of the nanoparticles or may be in close proximity to the nanoparticles (between about 0.2 and 1.0 nm). The skilled artisan will realize that it covalent attachment of the nucleotides to nanoparticles is not required in order to generate an enhanced Raman signal by SERS, SERRS or CARS.

In some embodiments of the invention, the nucleotides may be attached to nanoparticles as they travel down a microfluidic channel to form nucleotide-nanoparticle complexes. In certain embodiments of the invention, the length of time available for the cross-linking reaction to occur may be limited. Such embodiments may utilize highly reactive cross-linking groups with rapid reaction rates, such as epoxide groups, azido groups, arylazido groups, triazine groups or diazo groups. In certain embodiments of the invention, the cross-linking groups may be photoactivated by exposure to intense light, such as a laser. For example, photoactivation of diazo or azido compounds results in the formation, respectively, of highly reactive carbene and nitrene moieties. In certain embodiments, the reactive groups may be selected so that they can only attach the nanoparticles to nucleotides, rather than cross-linking the nanoparticles to each other. The selection and preparation of reactive cross-linking groups capable of binding to nucleotides is known in the art. In alternative embodiments of the invention, nucleotides may themselves be covalently modified, for example with a sulfhydryl group that can attach to gold nanoparticles.

In certain embodiments of the invention, nanoparticles may be manipulated into microfluidic channels by any method known in the art, such as microfluidics, nanofluidics, hydrodynamic focusing or electro-osmosis. In some embodiments, use of charged linker compounds or charged nanoparticles may facilitate manipulation of nanoparticles through the use of electrical gradients.

Immobilization of Nucleic Acids

In certain embodiments of the invention, one or more nucleic acid molecules may be attached to a surface such as functionalized glass, silicon, silicate, PDMS (polydimethyl siloxane), polyvinylidene difluoride (PVDF), silver or other metal coated surfaces, quartz, plastic, PTFE (polytetrafluoroethylene), PVP (polyvinyl pyrrolidone), poly(vinyl chloride), poly(methyl methacrylate), poly(dimethyl siloxane), polystyrene, polypropylene, polyacrylamide, latex, nylon, nitrocellulose, glass beads, magnetic beads, photopolymers which contain photoreactive species such as nitrenes, carbenes and ketyl radicals capable of forming covalent links with nucleic acid molecules (see U.S. Pat. Nos. 5,405,766 and 5,986,076) or any other material known in the art that is capable of having functional groups such as amino, carboxyl, thiol, hydroxyl or Diels-Alder reactants incorporated on its surface.

In some embodiments of the invention, the surface functional groups may be covalently attached to cross-linking compounds so that binding interactions between nucleic acid molecule and exonuclease and/or polymerase may occur without steric hindrance. Typical cross-linking groups include ethylene glycol oligomers and diamines. Attachment may be by either covalent or non-covalent binding. Various methods of attaching nucleic acid molecules to surfaces are known in the art and may be employed. In certain embodiments of the invention, the nucleic acid molecule is fixed in place and immersed in a microfluidic flow down a flow path and/or microfluidic channel that transports the released nucleotides past a detection unit. In non-limiting examples, the microfluidic flow may result from a bulk flow of solvent down a flow path and/or microfluidic channel.

In alternative embodiments of the invention, the bulk medium moves only slowly or not at all, but charged species within the solution (such as negatively charged nucleotides) move down a flow path and/or microfluidic channel in response to an externally applied electrical field.

Immobilization of nucleic acid molecules may be achieved by a variety of known methods. In an exemplary embodiment of the invention, immobilization may be achieved by coating a surface with streptavidin or avidin and the subsequent attachment of a biotinylated nucleic acid (Holmstrom et al., *Anal. Biochem.* 209:278–283, 1993). Immobilization may also occur by coating a silicon, glass or other surface with poly-L-Lys (lysine) or poly L-Lys, Phe (phenylalanine), followed by covalent attachment of either amino- or sulfhydryl-modified nucleic acids using bifunctional crosslinking reagents (Running et al., *BioTechniques* 8:276–277, 1990; Newton et al., *Nucleic Acids Res.* 21:1155–62, 1993). Amine residues may be coated on a surface through the use of aminosilane.

Immobilization may take place by direct covalent attachment of 5'-phosphorylated nucleic acids to chemically modified surfaces (Rasmussen et al., *Anal. Biochem.* 198:138-142, 1991). The covalent bond between the nucleic acid and the surface may be formed by condensation with a water-soluble carbodiimide. This method facilitates a predominantly 5'-attachment of the nucleic acids via their 5'-phosphates.

DNA is commonly bound to glass by first silanizing the glass surface, then activating with carbodiimide or glutaraldehyde. Alternative procedures may use reagents such as 3-glycidoxypropyltrimethoxysilane (GOP) or aminopropyltrimethoxysilane (APTS) with DNA linked via amino linkers incorporated at either the 3' or 5' end of the molecule. DNA may be bound directly to membrane surfaces using ultraviolet radiation. Other non-limiting examples of immobilization techniques for nucleic acids are disclosed in U.S. Pat. Nos. 5,610,287, 5,776,674 and 6,225,068.

Bifunctional cross-linking reagents may be of use in various embodiments of the invention, such as attaching a nucleic acid molecule to a surface. The bifunctional cross-linking reagents can be divided according to the specificity of their functional groups, e.g., amino, guanidino, indole, or carboxyl specific groups. Exemplary methods for cross-linking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

Nucleic Acid Synthesis

Polymerases

Certain embodiments of the invention involve binding of a synthetic reagent, such as a DNA polymerase, to a primer molecule and the addition of Raman labeled nucleotides to the 3' end of the primer. Non-limiting examples of polymerases include DNA polymerases, RNA polymerases, reverse transcriptases, and RNA-dependent RNA polymerases. The differences between these polymerases in terms of their "proofreading" activity and requirement or lack of requirement for primers and promoter sequences are known in the art. Where RNA polymerases are used as the polymerase, a template molecule to be sequenced may be double-stranded DNA. Non-limiting examples of polymerases include *Thermatoga maritima* DNA polymerase, AmplitaqFS™ DNA polymerase, Taquenase™ DNA polymerase, ThermoSequenase™, Taq DNA polymerase, Qbeta™ replicase, T4 DNA polymerase, *Thermus thermophilus* DNA polymerase, RNA-dependent RNA polymerase and SP6 RNA polymerase.

A number of polymerases are commercially available, including Pwo DNA Polymerase (Boehringer Mannheim Biochemicals, Indianapolis, Ind.); Bst Polymerase (Bio-Rad Laboratories, Hercules, Calif.); IsoTherm™ DNA Polymerase (Epicentre Technologies, Madison, Wis.); Moloney Murine Leukemia Virus Reverse Transcriptase, Pfu DNA Polymerase, Avian Myeloblastosis Virus Reverse Transcriptase, *Thermus flavus* (Tfl) DNA Polymerase and *Thermococcus litoralis* (Tli) DNA Polymerase (Promega Corp., Madison, Wis.); RAV2 Reverse Transcriptase, HIV-1 Reverse Transcriptase, T7 RNA Polymerase, T3 RNA Polymerase, SP6 RNA Polymerase, *E. coli* RNA Polymerase, *Thermus aquaticus* DNA Polymerase, T7 DNA Polymerase ±3'→5' exonuclease, Klenow Fragment of DNA Polymerase I, Thermus 'ubiquitous' DNA Polymerase, and DNA polymerase I (Amersham Pharmacia Biotech, Piscataway, N.J.). Any polymerase known in the art capable of template dependent polymerization of labeled nucleotides may be used. (See, e.g., Goodman and Tippin, Nat. Rev. Mol. Cell Biol. 1(2):101–9, 2000; U.S. Pat. No. 6,090,589.) Methods of using polymerases to synthesize nucleic acids from labeled nucleotides are known (e.g., U.S. Pat. Nos. 4,962,037; 5,405,747; 6,136,543; 6,210,896).

Primers

Generally, primers are between ten and twenty bases in length, although longer primers may be employed. In certain embodiments of the invention, primers are designed to be complementary in sequence to a known portion of a template nucleic acid molecule. Known primer sequences may be used, for example, where primers are selected for identifying sequence variants adjacent to known constant chromosomal sequences, where an unknown nucleic acid sequence is inserted into a vector of known sequence, or where a native nucleic acid has been partially sequenced. Methods for synthesis of primers of any sequence are known. Other embodiments of the invention involve sequencing a nucleic acid in the absence of a known primer-binding site. In such cases, it may be possible to use random primers, such as random hexamers or random oligomers to initiate polymerization.

Nucleic Acid Digestion

In certain embodiments of the invention, methods of nucleic acid sequencing involve binding of an exonuclease or equivalent reagent to the free end of a nucleic acid molecule and removal of nucleotides one at a time. Non-limiting examples of nucleic acid digesting enzymes of potential use include E. coli exonuclease I, III, V or VII, Bal 31 exonuclease, mung bean nuclease, S1 nuclease, E. coli DNA polymerase I holoenzyme or Klenow fragment, RecJ, exonuclease T, T4 or T7 DNA polymerase, Taq polymerase, exonuclease T7 gene 6, snake venom phosphodiesterase, spleen phosphodiesterase, *Thermococcus litoralis* DNA polymerase, Pyrococcus sp. GB-D DNA polymerase, lambda exonuclease, *S. aureus* micrococcal nuclease, DNase I, ribonuclease A, T1 micrococcal nuclease, or other exonucleases known in the art. Exonucleases are available from commercial sources such as New England Biolabs (Beverly, Mass.), Amersham Pharmacia Biotech (Piscataway, N.J.), Promega (Madison, Wis.), Sigma Chemicals (St. Louis, Mo.) or Boehringer Mannheim (Indianapolis, Ind.).

The skilled artisan will realize that enzymes with exonuclease activity may remove nucleotides from the 5' end, the 3' end, or either end of nucleic acid molecules. They can show specificity for RNA, DNA or both RNA and DNA. Their activity may depend on the use of either single or double-stranded nucleic acids. They may be differentially affected by salt concentration, temperature, pH, or divalent cations. These and other properties of exonucleases are known in the art. In certain embodiments of the invention, the rate of exonuclease activity may be manipulated to coincide with the optimal rate of analysis of nucleotides by the detection unit. Various methods are known for adjusting the rate of exonuclease activity, including adjusting the temperature, pressure, pH, salt or divalent cation concentration in a reaction chamber.

Although nucleoside monophosphates will generally be released from nucleic acids by exonuclease activity, the embodiments of the invention are not limited to detection of any particular form of free nucleotide or nucleoside but encompass any monomer that may be released from a nucleic acid.

Reaction Chamber and Integrated Chip

Some embodiments of the invention concern apparatus comprising a reaction chamber designed to contain an immobilization surface, nucleic acid molecule, exonuclease and nucleotides in an aqueous environment. In some embodiments of the invention, the reaction chamber may be temperature controlled, for example by incorporation of Pelletier elements or other methods known in the art. Methods of controlling temperature for low volume liquids are known. (See, e.g., U.S. Pat. Nos. 5,038,853, 5,919,622, 6,054,263 and 6,180,372.)

In certain embodiments of the invention, the reaction chamber and any associated fluid channels, for example, a flow path, microfluidic channels or channels to provide connections to waste ports, to a nucleic acid loading port, to a nanoparticle reservoir, to a source of exonuclease or other fluid compartments are manufactured in a batch fabrication process, as known in the fields of computer chip manufacture and/or microcapillary chip manufacture. In some embodiments of the invention, the reaction chamber and other components of the apparatus, such as the flow path and/or microfluidic channels, may be manufactured as a single integrated chip. Such a chip may be manufactured by methods known in the art, such as by photolithography and etching. However, the manufacturing method is not limiting and other methods known in the art may be used, such as laser ablation, injection molding, casting, molecular beam epitaxy, dip-pen nanolithograpy, chemical vapor deposition (CVD) fabrication, electron beam or focused ion beam technology or imprinting techniques. Methods for manufacture of nanoelectromechanical systems may be used for certain embodiments of the invention. (See, e.g., Craighead, Science 290:1532–36, 2000.) Microfabricated chips are commercially available from, e.g., Caliper Technologies Inc. (Mountain View, Calif.) and ACLARA BioSciences Inc. (Mountain View, Calif.).

To facilitate detection of nucleotides by the detection unit the material comprising the flow path or flow-through cell may be selected to be transparent to electromagnetic radiation at the excitation and emission frequencies used for the detection unit. Glass, silicon, and any other materials that are generally transparent in the wavelengths used for Raman spectroscopy may be used. In some embodiments of the invention the surfaces of the flow path or flow-through cell that are opposite the detection unit may be coated with silver, gold, platinum, copper, aluminum or other materials that are relatively opaque to the detection unit. In that position, the opaque material is available to enhance the Raman signal, for example by SERS, while not interfering with the function of the detection unit. Alternatively, the flow path or flow-through cell may contain a mesh comprising silver, gold, platinum, copper, aluminum or other Raman signal enhancing metal. In other alternative embodiments of the invention, the flow path or flow-through cell may contain metal nanoparticles.

Flow Path and Microfluidic Channels

In certain embodiments of the invention, the nucleotides released from a nucleic acid are moved down a flow path and/or microfluidic channels past a detection unit. A non-limiting example of techniques for transport of nucleotides includes microfluidic techniques. The flow path and/or microfluidic channels can comprise a microcapillary (e.g., from ACLARA BioSciences Inc., Mountain View, Calif.) or a liquid integrated circuit (e.g., Caliper Technologies Inc., Mountain View, Calif.). A microchannel flow path may be from about 5 to 200 μm in diameter, with a diameter of about 5, 10, 15, 20, 25, 30, 35, 40, 45, 50, 55, 60, 65, 70, 75, 80, 90, 100, 110, 120, 130, 140, 150, 160, 170, 180, 190 or 200 μm.

In certain embodiments of the invention, the nucleotides to be detected move down the flow path and/or microfluidic channels by bulk flow of solvent. In other embodiments of the invention, microcapillary electrophoresis may be used to transport nucleotides down the flow path and/or microfluidic channels. Microcapillary electrophoresis generally involves the use of a thin capillary or channel that may or may not be filled with a particular separation medium. Electrophoresis of appropriately charged molecular species, such as negatively charged nucleotides, occurs in response to an imposed electrical field, negative on the reaction chamber side of the apparatus and positive on the detection unit side. Although electrophoresis is often used for size separation of a mixture of components that are simultaneously added to the microcapillary, it can also be used to transport similarly sized nucleotides that are sequentially released from a nucleic acid. Because the purine nucleotides (A, G) are larger than the pyrimidine nucleotides (C, T, U) and would therefore migrate more slowly, the length of the flow path and/or microfluidic channels and the corresponding transit time past the detection unit may kept to a minimum to prevent differential migration from mixing up the order of nucleotides released from the nucleic acid. Alternatively, the medium filling the microcapillary may be selected so that the migration rates of purine and pyrimidine nucleotides down the flow path and/or microfluidic channels are similar or identical. Methods of microcapillary electrophoresis have been disclosed, for example, by Woolley and Mathies (*Proc. Natl. Acad. Sci. USA* 91:11348–352, 1994).

In certain embodiments of the invention, flow paths and/or microfluidic channels may contain aqueous solutions with relatively high viscosity, such as glycerol solutions. Such high viscosity solutions may serve to decrease the flow rate and increase the reaction time available, for example, for cross-linking nucleotides to nanoparticles.

Microfabrication of microfluidic devices, including microcapillary electrophoretic devices has been disclosed in, e.g., Jacobsen et al. (*Anal. Biochem*, 209:278–283,1994); Effenhauser et al. (*Anal. Chem.* 66:2949–2953, 1994); Harrison et al. (Science 261:895–897, 1993) and U.S. Pat. No. 5,904,824. These methods may comprise micromolding techniques with silicon masters made using standard photolithography or focused ion beam techniques, or photolithographic etching of micron scale channels on silica, silicon or other crystalline substrates or chips. Such techniques may be readily adapted for use in the disclosed methods and apparatus. In some embodiments of the invention, the microcapillary may be fabricated from the same materials used for fabrication of a reaction chamber, using techniques known in the art.

Detection Unit

In various embodiments of the invention, the detection unit is designed to detect and quantify nucleotides by Raman spectroscopy. Methods for detection of micromolar concentrations of nucleotides by Raman spectroscopy are known in the art. (See, e.g., U.S. Pat. Nos. 5,306,403; 6,002,471; 6,174,677). Exemplary methods for detection of nucleotides at the single molecule level are disclosed in the Examples below. Variations on surface enhanced Raman spectroscopy (SERS), surface enhanced resonance Raman spectroscopy (SERRS) and coherent anti-Stokes Raman spectroscopy (CARS) have been disclosed. The sensitivity of Raman detection is enhanced by a factor of $10^6$ or more for molecules adjacent to roughened metal surfaces, such as silver, gold, platinum, copper or aluminum surfaces.

A non-limiting example of a Raman detection unit is disclosed in U.S. Pat. No. 6,002,471. An excitation beam is generated by either a frequency doubled Nd:YAG laser at 532 nm wavelength or a frequency doubled Ti:sapphire laser at 365 nm wavelength. Pulsed laser beams or continuous laser beams may be used. The excitation beam passes through confocal optics and a microscope objective, and is focused onto the flow path and/or the flow-through cell. The Raman emission light from the nucleotides is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector, comprising an avalanche photodiode interfaced with a computer for counting and digitization of the signal.

Another example of a Raman detection unit is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source comprises a 514.5 nm line argon-ion laser from SpectraPhysics, Model 166, and a 647.1 nm line of a krypton-ion laser (Innova 70, Coherent).

Alternative excitation sources include a nitrogen laser (Laser Science Inc.) at 337 nm and a helium-cadmium laser (Liconox) at 325 nm (U.S. Pat. No. 6,174,677), a light emitting diode, an Nd:YLF laser, and/or various ions lasers and/or dye lasers. The excitation beam may be spectrally purified with a bandpass filter (Corion) and may be focused on the flow path and/or flow-through cell using a 6× objective lens (Newport, Model L6X). The objective lens may be used to both excite the nucleotides and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection of nucleotides, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Information Processing and Control System and Data Analysis

In certain embodiments of the invention, the nucleic acid sequencing apparatus may comprise an information processing system. The disclosed methods and apparatus are not limiting for the type of information processing system used. An exemplary information processing system may incorporate a computer comprising a bus for communicating information and a processor for processing information. In one embodiment of the invention, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, or a Pentium Xeon® processor (Intel Corp., Santa Clara, Calif.). In various other embodiments of the invention, the processor may be based on Intel® architecture, such as Intel® IA-32 or Intel® IA-64 architecture. Alternatively, other processors may be used. The information processing and control system may further comprise any peripheral devices known in the art, such as memory, display, keyboard and/or other devices.

In particular embodiments of the invention, the detection unit may be operably coupled to the information processing system. Data from the detection unit may be processed by the processor and data stored in memory. Data on emission profiles for standard nucleotides may also be stored in memory. The processor may compare the emission spectra from nucleotides in the flow path and/or flow-through cell to identify the type of nucleotide released from the nucleic acid molecule. The memory may also store the sequence of nucleotides released from the nucleic acid molecule. The processor may analyze the data from the detection unit to determine the sequence of the nucleic acid. The information processing system may also perform standard procedures such as subtraction of background signals and "base-calling" determination when overlapping signals are detected.

While the disclosed methods may be performed under the control of a programmed processor, in alternative embodiments of the invention, the methods may be fully or partially implemented by any programmable or hardcoded logic, such as Field Programmable Gate Arrays (FPGAs), TTL logic, or Application Specific Integrated Circuits (ASICs). Additionally, the disclosed methods may be performed by any combination of programmed general purpose computer components and/or custom hardware components.

Following the data gathering operation, the data will typically be reported to a data analysis operation. To facilitate the analysis operation, the data obtained by the detection unit will typically be analyzed using a digital computer such as that described above. Typically, the computer will be appropriately programmed for receipt and storage of the data from the detection unit as well as for analysis and reporting of the data gathered.

In certain embodiments of the invention, custom designed software packages may be used to analyze the data obtained from the detection unit. In alternative embodiments of the invention, data analysis may be performed, using an information processing system and publicly available software packages. Non-limiting examples of available software for DNA sequence analysis include the PRISM™ DNA Sequencing Analysis Software (Applied Biosystems, Foster City, Calif.), the Sequencher™ package (Gene Codes, Ann Arbor, Mich.), and a variety of software packages available through the National Biotechnology Information Facility at website www.nbif.org/links/1.4.1.php.

EXAMPLES

Example 1

Raman Detection of Nucleotides

Methods and Apparatus

In a non-limiting example, the excitation beam of a Raman detection unit was generated by a titanium:sapphire laser (Mira by Coherent) at a near-infrared wavelength (750~950 nm) or a gallium aluminum arsenide diode laser (PI-ECL series by Process Instruments) at 785 nm or 830 nm. Pulsed laser beams or continuous beams were used. The excitation beam was reflected by a dichroic mirror (holographic notch filter by Kaiser Optical or a dichromatic interference filter by Chroma or Omega Optical) into a collinear geometry with the collected beam. The reflected beam passed through a microscope objective (Nikon LU series), and was focused onto the Raman active substrate where target analytes (nucleotides or purine or pyrimidine bases) were located.

The Raman scattered light from the analytes was collected by the same microscope objective, and passed the dichroic mirror to the Raman detector. The Raman detector comprised a focusing lens, a spectrograph, and an array detector. The focusing lens focused the Raman scattered light through the entrance slit of the spectrograph. The spectrograph (Acton Research) comprised a grating that dispersed the light by its wavelength. The dispersed light was imaged onto an array detector (back-illuminated deep-depletion CCD camera by RoperScientific). The array detector was connected to a controller circuit, which was connected to a computer for data transfer and control of the detector function.

For surface-enhanced Raman spectroscopy (SERS), the Raman active substrate consisted of metallic nanoparticles or metal-coated nanostructures. Silver nanoparticles, ranging in size from 5 to 200 nm, was made by the method of Lee and Meisel (*J. Phys. Chem.*, 86:3391, 1982). Alternatively, samples were placed on an aluminum substrate under the microscope objective. The Figures discussed below were collected in a stationary sample on the aluminum substrate. The number of molecules detected was determined by the optical collection volume of the illuminated sample.

The ability to detect single nucleotides by SERS was confirmed using a 100 µm or 200 µm microfluidic channel. In various embodiments of the invention, nucleotides may be delivered to a Raman active substrate through a microfluidic channel (between about 5 and 200 µm wide). Microfluidic channels can be made by molding polydimethylsiloxane (PDMS), using the technique disclosed in Anderson et al. ("Fabrication of topologically complex three-dimensional microfluidic systems in PDMS by rapid prototyping," *Anal. Chem.* 72:3158–3164, 2000).

Where SERS was performed in the presence of silver nanoparticles, the nucleotide, purine or pyrimidine analyte was mixed with LiCl (90 µM final concentration) and nanoparticles (0.25 M final concentration silver atoms). SERS data were collected using room temperature analyte solutions.

Results

Nucleoside monophosphates, purine bases and pyrimidine bases were analyzed by SERS, using the system disclosed above. Table 1 shows the present detection limits for various analytes of interest.

TABLE 1

SERS Detection of Nucleoside Monophosphates, Purines and Pyrimidines

| Analyte | Final Concentration | Number of Molecules Detected |
|---|---|---|
| dAMP | 9 picomolar (pM) | ~1 molecule |
| Adenine | 9 pM | ~1 molecule |
| dGMP | 90 µM | 6 × 10$^6$ |
| Guanine | 909 pM | 60 |
| dCMP | 909 µM | 6 × 10$^7$ |
| Cyotosine | 90 nM | 6 × 10$^3$ |

TABLE 1-continued

SERS Detection of Nucleoside Monophosphates, Purines and Pyrimidines

| Analyte | Final Concentration | Number of Molecules Detected |
|---|---|---|
| dTMP | 9 μM | $6 \times 10^5$ |
| Thymine | 90 nM | $6 \times 10^3$ |

Conditions were optimized for adenine nucleotides only. LiCL (90 μM final concentration) was determined to provide optimal SERS detection of adenine nucleotides. Detection of other nucleotides may be facilitated by use of other alkali-metal halide salts, such as NaCl, KCl, RbCl or CsCl. The claimed methods are not limited by the electrolyte solution used, and it is contemplated that other types of electrolyte solutions, such as MgCl, CaCl, NaF, KBr, LiI, etc. may be of use. The skilled artisan will realize that electrolyte solutions that do not exhibit strong Raman signals will provide minimal interference with SERS detection of nucleotides. The results demonstrate that the Raman detection system and methods disclosed above were capable of detecting and identifying single molecules of nucleotides and purine bases. This is the first report of Raman detection of unlabeled nucleotides at the single nucleotide level.

Example 2

Raman Emission Spectra of Nucleotides, Purines and Pyrimidines

Figure 4:
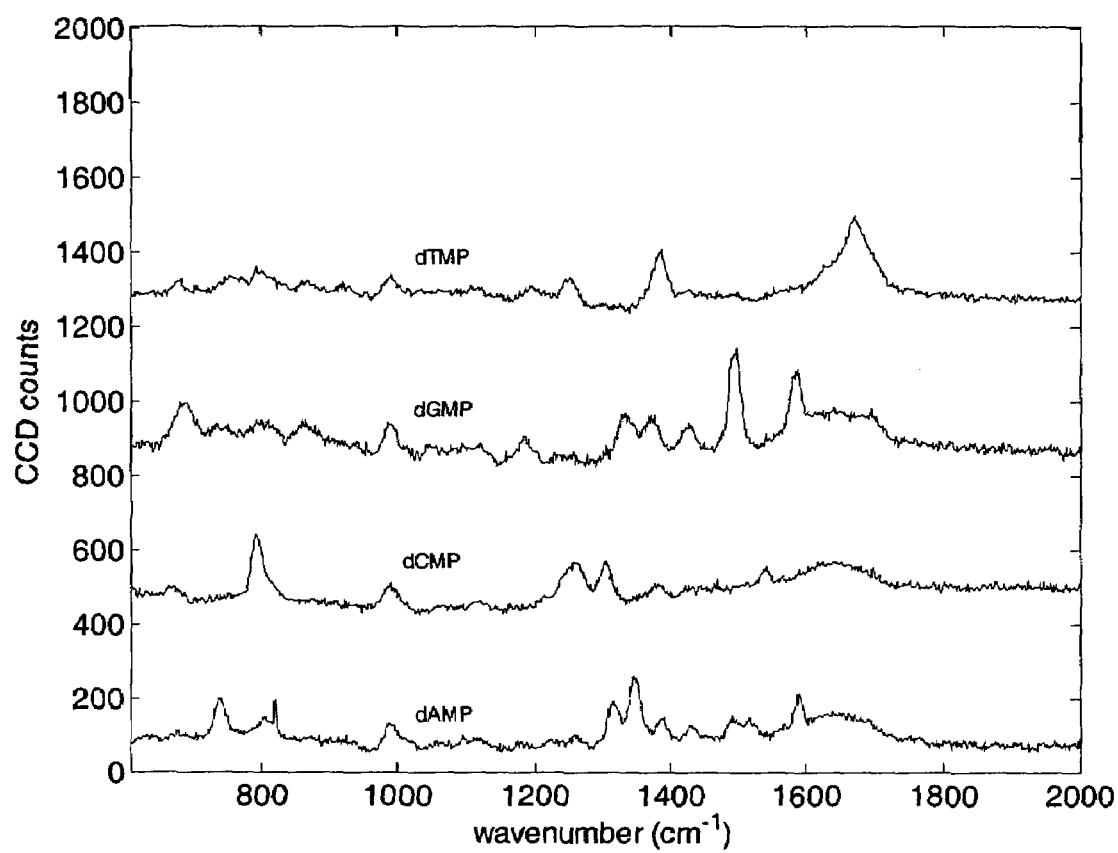
FIG. 4 shows the Raman spectra of all four deoxynucleoside monophosphates (dNTPs) at 100 mM concentration, using a 100 millisecond data collection time. Characteristic Raman emission peaks for as shown for each different type of nucleotide. The data were collected without surface-enhancement or labeling of the nucleotides.

The Raman emission spectra of various analytes of interest was obtained using the protocol of Example 1, with the indicated modifications. FIG. 4 shows the Raman emission spectra of a 100 mM solution of each of the four nucleoside monophosphates, in the absence of surface enhancement and without Raman labels. No LiCl was added to the solution. A 100 millisecond (msec) data collection time was used. Lower concentrations of nucleotides may be detected with longer collection times. Excitation occurred at 514 nm. For each of the following figures, a 785 nm excitation wavelength was used. As shown in FIG. 4, the unenhanced Raman spectra showed characteristic emission peaks for each of the four unlabeled nucleoside monophosphates.

Figure 5:
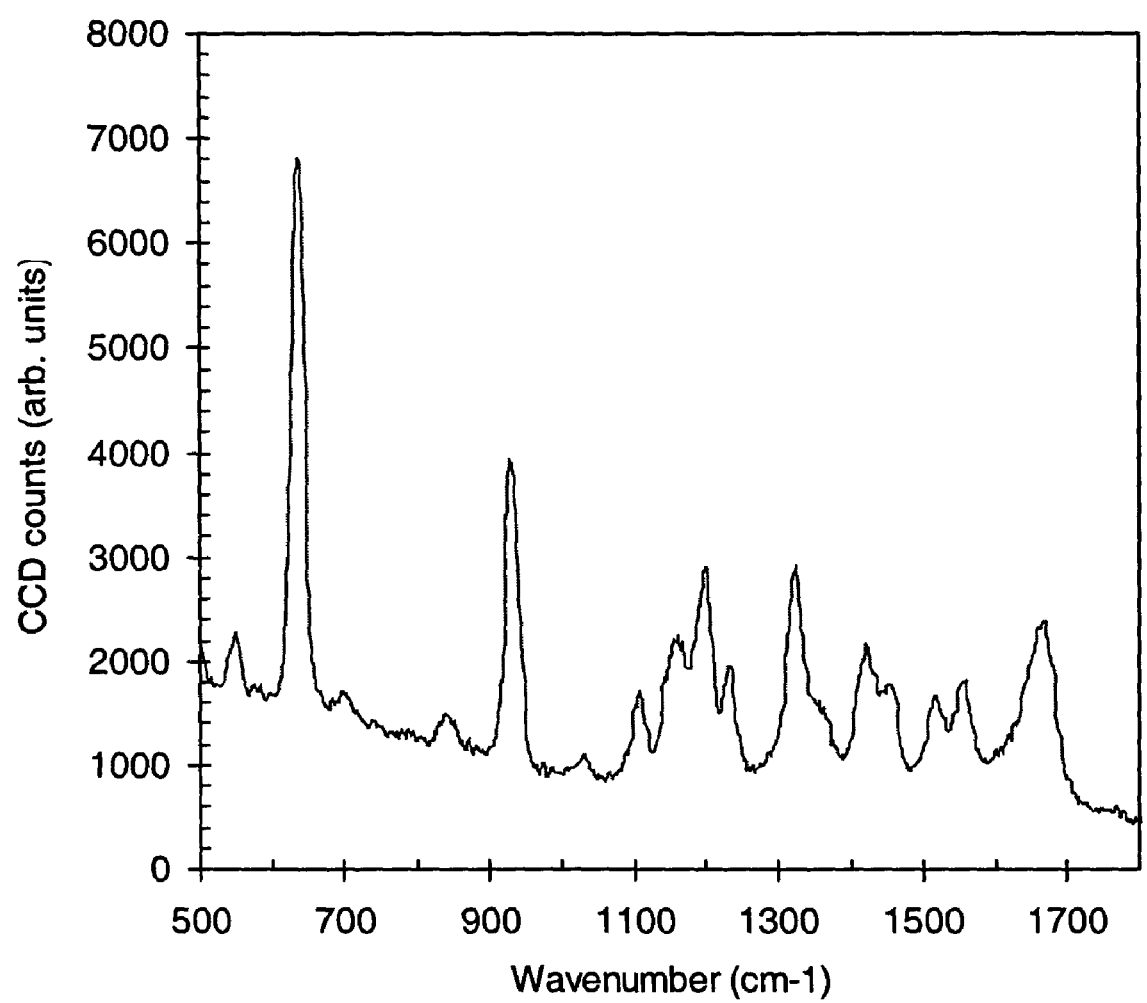
FIG. 5 shows SERS detection of 1 nM guanine, obtained from dGMP by acid treatment according to Nucleic Acid Chemistry, Part 1, L. B. Townsend and R. S. Tipson (Eds.), Wiley-Interscience, New York, 1978.

FIG. 5 shows the SERS spectrum of a 1 nm solution of guanine, in the presence of LiCl and silver nanoparticles. Guanine was obtained from dGMP by acid treatment, as discussed in *Nucleic Acid Chemistry, Part* 1, L. B. Townsend and R. S. Tipson (eds.), Wiley-Interscience, New York, 1978. The SERS spectrum was obtained using a 100 msec data collection time.

Figure 6:
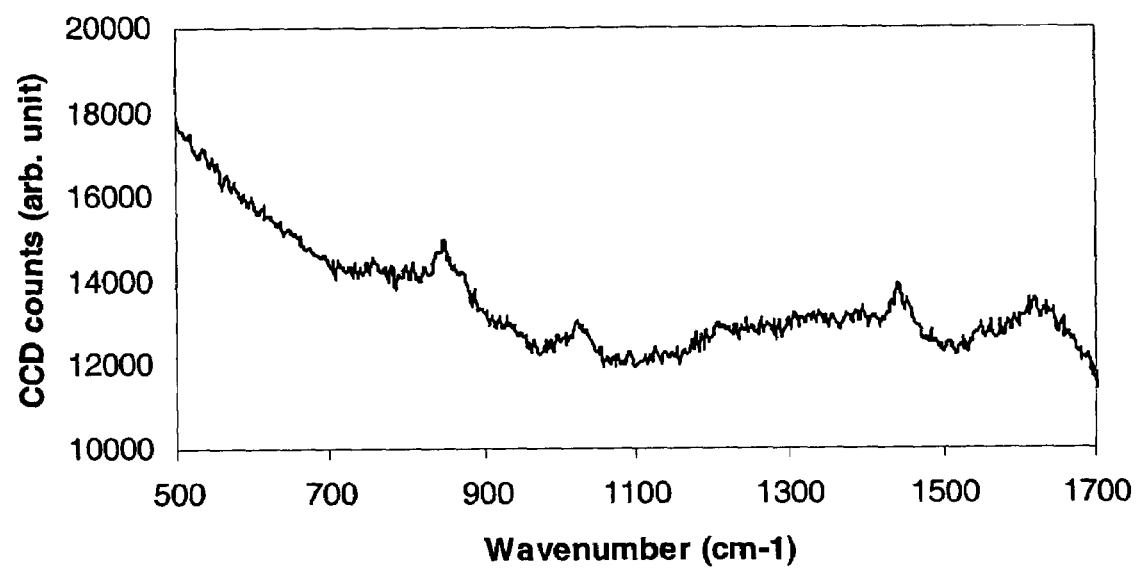
FIG. 6 shows SERS detection of 10 nM cytosine, obtained from dCMP by acid treatment.

FIG. 6 shows the SERS spectrum of a 10 nM cytosine solution, obtained from dCMP by acid hydrolysis. Data were collected using a 1 second collection time.

Figure 7:
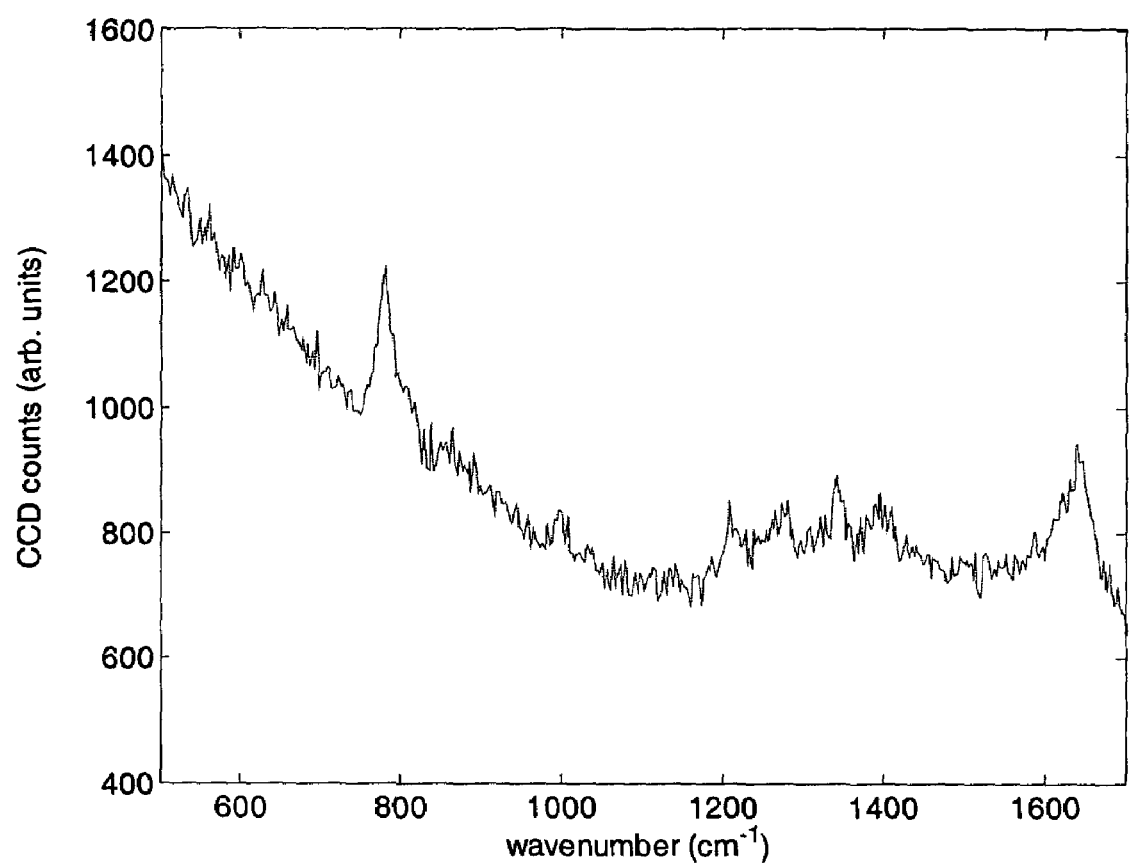
FIG. 7 shows SERS detection of 100 nM thymine, obtained from dTMP by acid treatment.

FIG. 7 shows the SERS spectrum of a 100 nM thymine solution, obtained by acid hydrolysis of dTMP. Data were collected using a 100 msec collection time.

Figure 8:
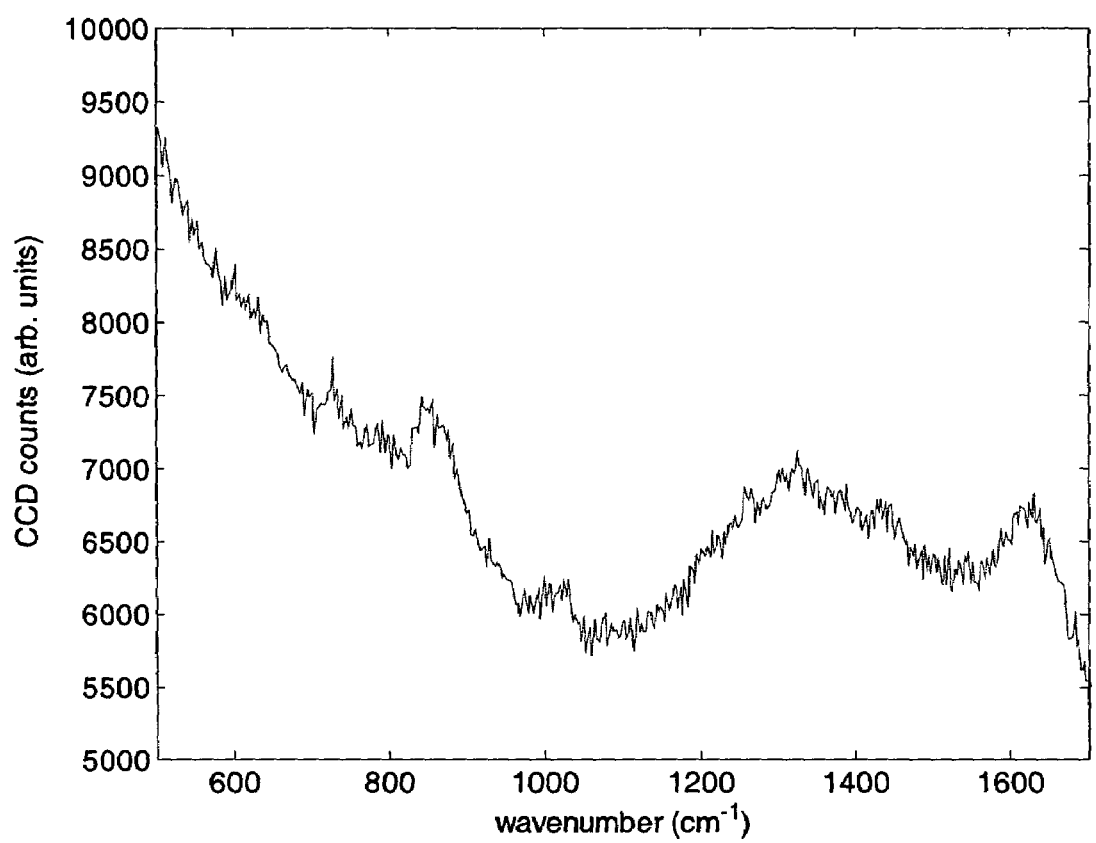
FIG. 8 shows SERS detection of 100 pM adenine, obtained from dAMP by acid treatment.

FIG. 8 shows the SERS spectrum of a 100 pM adenine solution, obtained by acid hydrolysis of dAMP. Data were collected for 1 second.

Figure 9:
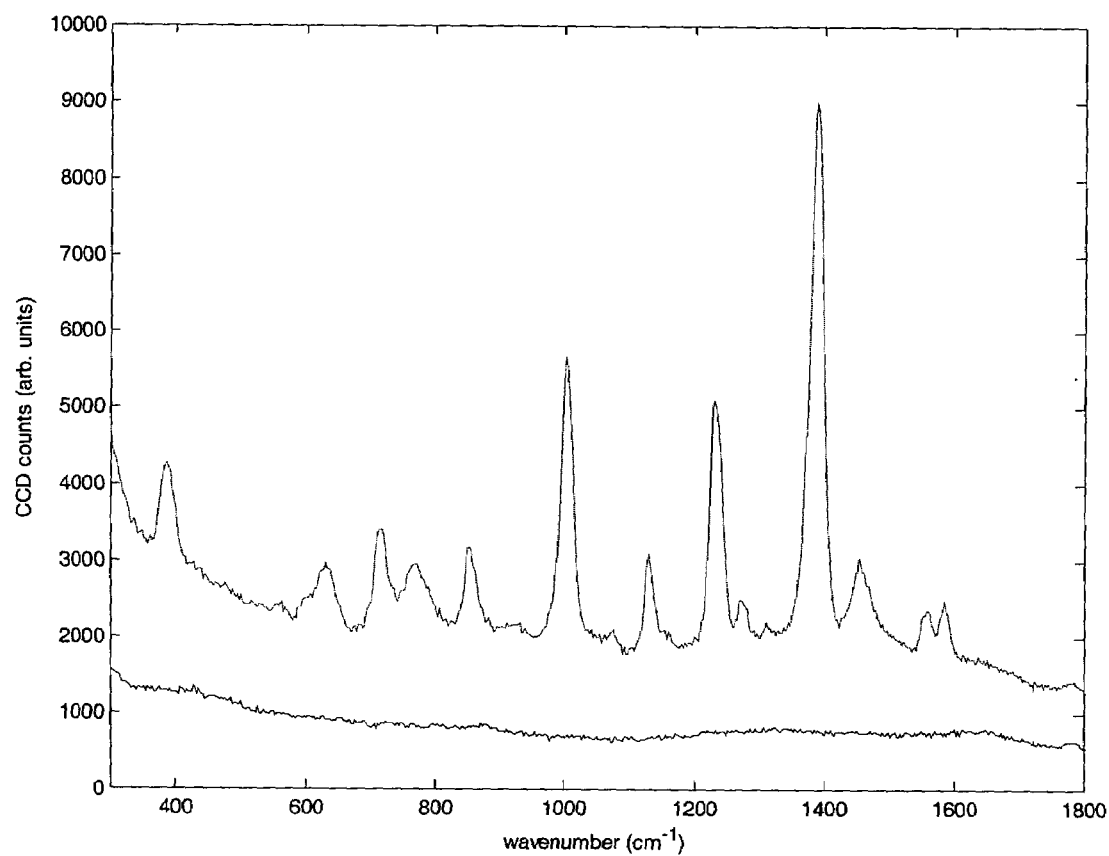
FIG. 9 shows a comparative SERS spectrum of a 500 nM solution of deoxyadenosine triphosphate covalently labeled with fluorescein (upper trace) and unlabeled dATP (lower trace). The dATP-fluorescein was obtained from Roche Applied Science (Indianapolis, Ind.). A strong increase in the SERS signal was detected in the fluorescein labeled dATP.

FIG. 9 shows the SERS spectrum of a 500 nM solution of dATP (lower trace) and fluorescein-labeled dATP (upper trace). dATP-fluorescein was purchased from Roche Applied Science (Indianapolis, Ind.). The Figure shows a strong increase in SERS signal due to labeling with fluorescein.

Example 3

SERS Detection of Nucleotides and Amplification Products

Silver Nanoparticle Formation

Silver nanoparticles used for SERS detection were produced according to Lee and Meisel (1982). Eighteen milligrams of $AgNO_3$ were dissolved in 100 mL (milliliters) of distilled water and heated to boiling. Ten mL of a 1% sodium citrate solution was added drop-wise to the $AgNO_3$ solution over a 10 min period. The solution was kept boiling for another hour. The resulting silver colloid solution was cooled and stored.

SERS Detection of Adenine

Figure 10:
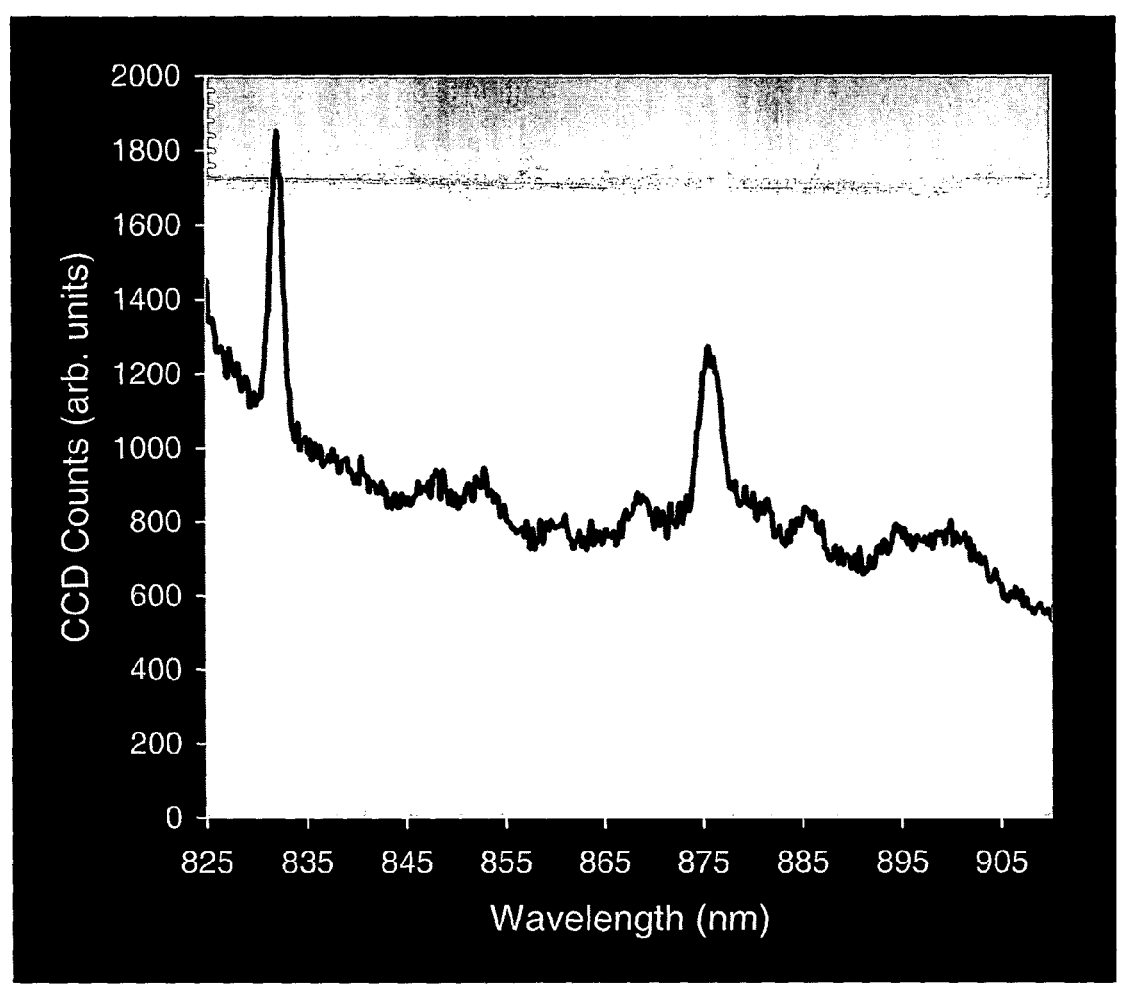
FIG. 10 shows the SERS detection of a 0.9 nM (nanomolar) solution of adenine. The detection volume was 100 to 150 femtoliters, containing an estimated 60 molecules of adenine.

The Raman detection system was as disclosed in Example 1. One mL of silver colloid solution was diluted with 2 mL of distilled water. The diluted silver colloid solution (160 μL) (microliters) was mixed with 20 μL of a 10 nM (nanomolar) adenine solution and 40 μL of LiCl (0.5 molar) on an aluminum tray. The LiCl acted as a Raman enhancing agent for adenine. The final concentration of adenine in the sample was 0.9 nM, in a detection volume of about 100 to 150 femtoliters, containing an estimated 60 molecules of adenine. The Raman emission spectrum was collected using an excitation source at 785 nm excitation, with a 100 millisecond collection time. As shown in FIG. 10, this procedure demonstrated the detection of 60 molecules of adenine, with strong emission peaks detected at about 833 nm and 877 nm. As discussed in Example 1, single molecule detection of adenine has been shown using the disclosed methods and apparatus.

Rolling Circle Amplification

One picomole (pmol) of a rolling circle amplification (RCA) primer was added to 0.1 pmol of circular, single-stranded M13 DNA template. The mixture was incubated with 1× T7 polymerase 160 buffer (20 mM (millimolar) Tris-HCl, pH 7.5, 10 mM $MgCl_2$, 1 mM dithiothreitol), 0.5 mM dNTPs and 2.5 units of T7 DNA polymerase for 2 hours at 37° C., resulting in formation of an RCA product. A negative control was prepared by mixing and incubating the same reagents without the DNA polymerase.

SERS Detection of RCA Product

One μL of the RCA product and 1 μL of the negative control sample were separately spotted on an aluminum tray and air-dried. Each spot was rinsed with 5 μL of 1× PBS (phosphate buffered saline). The rinse was repeated three times and the aluminum tray was air-dried after the final rinse.

Figure 11:
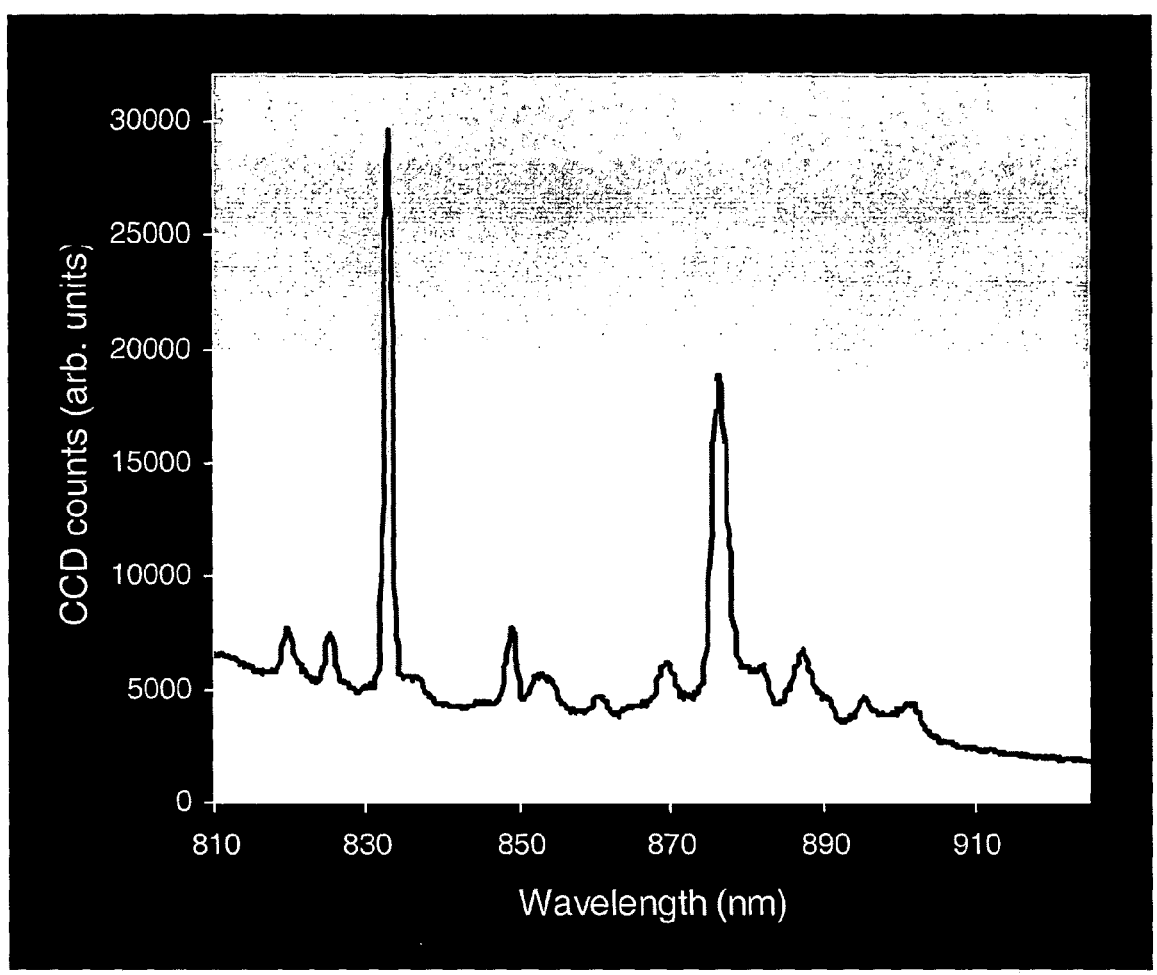
FIG. 11 shows the SERS detection of a rolling circle amplification product, using a single-stranded, circular M13 DNA template.

One milliliter of silver colloid solution prepared as above was diluted with 2 mL of distilled water. Eight microliters of the diluted silver colloid solution was mixed with 2 μL of 0.5 M LiCl and added to the RCA product spot on the aluminum tray. The same solution was added to the negative control spot. The Raman signals were collected as disclosed above. As demonstrated in FIG. 11, an RCA product was detectable by SERS, with emission peaks at about 833 and 877 nm. Under the conditions of this protocol, with an LiCl enhancer, the signal strength from the adenine moieties is stronger than those for guanine, cytosine and thymine. The negative control (not shown) showed that the Raman signal was specific for the RCA product, as no signal was observed in the absence of amplification.

Example 4

Exonuclease Digestion of Nucleic Acids

Exonuclease treatment is performed according to Sauer et al. (*J. Biotech.* 86:181–201, 2001). Single nucleic acid molecules labeled on the 5' end with biotin are prepared by PCR amplification of a nucleic acid template, using a 5'-biotinylated oligonucleotide primer. A cone-shaped 3 μm single-mode optical fiber (SMC-A0630B, Laser Components GmbH, Olching, Germany) is prepared. The glass fiber is chemically etched with HF to form a sharp tip. After coating with 3-mercaptopropyltrimethoxysilane, the tip is treated with γ-maleinimidobutyric acid N-hydroxysuccinamide (GMBS). The tip of the fiber is activated with streptavidin and allowed to bind to the biotinylated DNA. Unbound DNA is removed by washing.

The fiber containing a single molecule of bound DNA is inserted into a PDMS reaction chamber attached to a 5 μm microchannel. Exonuclease I is added to the reaction chamber to initiate cleavage of the ssDNA. The exonuclease is confined to the reaction chamber by use of an optical trap (e.g. Walker et al., FEBS Lett. 459:39–42, 1999; Bennink et al., Cytometry 36:200–208, 1999; Mehta et al., Science 283:1689–95, 1999; Smith et al., Am. J. Phys. 67:26–35, 1999). Optical trapping devices are available from Cell Robotics, Inc. (Albuquerque, N.M.), S+L GmbH (Heidelberg, Germany) and P.A.L.M. Gmbh (Wolfratshausen, Germany). Nucleoside monophosphates are released by exonuclease digestion and transported past a Raman detector, as disclosed in Example 1, by microfluidic flow. A 90 μM concentration of LiCl is added to the detection mixture, and the microfluidic channel in the vicinity of the detector is packed with silver nanoparticles prepared according to Lee and Meisel (1982). Single nucleotides are detected as they flow past the Raman detector, allowing determination of the nucleic acid sequence.

Example 5

Nucleic Acid Sequencing Using Raman-Labeled Nucleotides

Certain embodiments of the invention are exemplified in FIG. 1. FIG. 1 illustrates methods and an apparatus 10 for sequencing individual single-stranded nucleic acid molecules 13 that are attached to an immobilization surface 14 in a reaction chamber 11 and disassembled in a deconstruction reaction. In such embodiments of the invention, the reaction chamber 11 contains one or more exonucleases 15 that sequentially remove one nucleotide 16 at a time from the unattached end 17 of the nucleic acid molecule 13.

As the nucleotides 16 are released, they move down a flow path 12 past a detection unit 18. The detection unit 18 comprises an excitation source 19, such as a laser, that emits an excitatory beam 20. The excitatory beam 20 interacts with the released nucleotides 16 so that electrons are excited to a higher energy state. The Raman emission spectrum that results from the return of the electrons to a lower energy state is detected by a Raman spectroscopic detector 21, such as a spectrometer, a monochromator or a charge coupled device (CCD), such as a CCD camera.

Preparation of Reaction Chamber and Flow Path

Borofloat glass wafers (Precision Glass & Optics, Santa Ana, Calif.) are pre-etched for a short period in concentrated HF (hydrofluoric acid) and cleaned before deposition of an amorphous silicon sacrificial layer in a plasma-enhanced chemical vapor deposition (PECVD) system (PEII-A, Technics West, San Jose, Calif.). Wafers are primed with hexamethyldisilazane (HMDS), spin-coated with photoresist (Shipley 1818, Marlborough, MA) and soft-baked. A contact mask aligner (Quintel Corp. San Jose, Calif.) is used to expose the photoresist layer with one or more mask designs, and the exposed photoresist removed using a mixture of Microposit developer concentrate (Shipley) and water. Developed wafers are hard-baked and the exposed amorphous silicon removed using $CF_4$ (carbon tetrafluoride) plasma in a PECVD reactor. Wafers are chemically etched with concentrated HF to produce the reaction chamber 11 and flow path 12. The remaining photoresist is stripped and the amorphous silicon removed. Using these methods, microchannels of about 50 to 100 μm diameter may be prepared. Smaller diameter channels may be prepared by known methods, such as coating the inside of the microchannel to narrow the diameter, or using nanolithography, focused electron beam, focused ion beam or focused atom laser techniques. Methods for making PDMS microchannels are discussed above.

Access holes are drilled into the etched wafers with a diamond drill bit (Crystalite, Westerville, Ohio). A finished chip is prepared by thermally bonding two complementary etched and drilled plates to each other in a programmable vacuum furnace (Centurion VPM, J. M. Ney, Yucaipa, Calif). Alternative exemplary methods for fabrication of a chip incorporating a reaction chamber 11 and flow path 12 are disclosed in U.S. Pat. Nos. 5,867,266 and 6,214,246. In certain embodiments of the invention, a nylon filter with a molecular weight cutoff of 2,500 daltons is inserted between the reaction chamber 11 and the flow path 12 to prevent exonuclease 15 from leaving the reaction chamber 11.

Nucleic Acid Preparation and Exonuclease Treatment

Human chromosomal DNA is purified according to Sambrook et al. (1989). Following digestion with Bam H1, the genomic DNA fragments are inserted into the multiple cloning site of the pBluescript® II phagemid vector (Stratagene, Inc., La Jolla, Calif.) and grown up in *E. coli*. After plating on ampicillin-containing agarose plates a single colony is selected and grown up for sequencing. Single-stranded DNA copies of the genomic DNA insert are rescued by co-infection with helper phage. After digestion in a solution of proteinase K:sodium dodecyl sulphate (SDS), the DNA is phenol extracted and then precipitated by addition of sodium acetate (pH 6.5, about 0.3 M) and 0.8 volumes of 2-propanol. The DNA containing pellet is resuspended in Tris-EDTA buffer and stored at −20° C. until use. Agarose gel electrophoresis shows a single band of purified DNA.

M13 forward primers complementary to the known pBluescript® sequence, located next to the genomic DNA insert, are purchased from Midland Certified Reagent Company (Midland, Tex.). The primers are covalently modified to contain a biotin moiety attached to the 5' end of the oligonucleotide. The biotin group is covalently linked to the 5'-phosphate of the primer via a $(CH_2)_6$ spacer. Biotin-labeled primers are allowed to hybridize to the ssDNA template molecules prepared from the pBluescript® vector. The primer-template complexes are then attached to streptavidin-coated beads 14 according to Dorre et al. (Bioimaging 5: 139–152, 1997). At appropriate DNA dilutions, a single primer-template complex is attached to a single bead 14. A bead 14 containing a single primer-template complex is inserted into the reaction chamber 11 of a sequencing apparatus 10.

The primer-template is incubated with modified T7 DNA polymerase (United States Biochemical Corp., Cleveland, Ohio). The reaction mixture contains unlabeled deoxyadenosine-5'-triphosphate (dATP) and deoxyguanosine-5'-triphosphate (dGTP), digoxigenin-labeled deoxyuridine-5'-triphosphate (digoxigenin-dUTP) and rhodamine-labeled deoxycytidine-5'-triphosphate (rhodamine-dCTP). The polymerization reaction is allowed to proceed for 2 hours at 37° C. After synthesis of the digoxigenin and rhodamine labeled nucleic acid 13, the template strand is separated from the labeled nucleic acid 13, and the template strand, DNA polymerase and unincorporated nucleotides are washed out of the reaction chamber 11.

Exonuclease 15 activity is initiated by addition of exonuclease III 15 to the reaction chamber 11. The reaction mixture is maintained at pH 8.0 and 37° C. As nucleotides 16 are released from the 3' end 17 of the nucleic acid 13, they are transported by microfluidic flow down the flow path 12 past the detection unit 18.

Example 6

Nucleic Acid Sequencing Using Covalent Attachment to Nanoparticles

Figure 2:
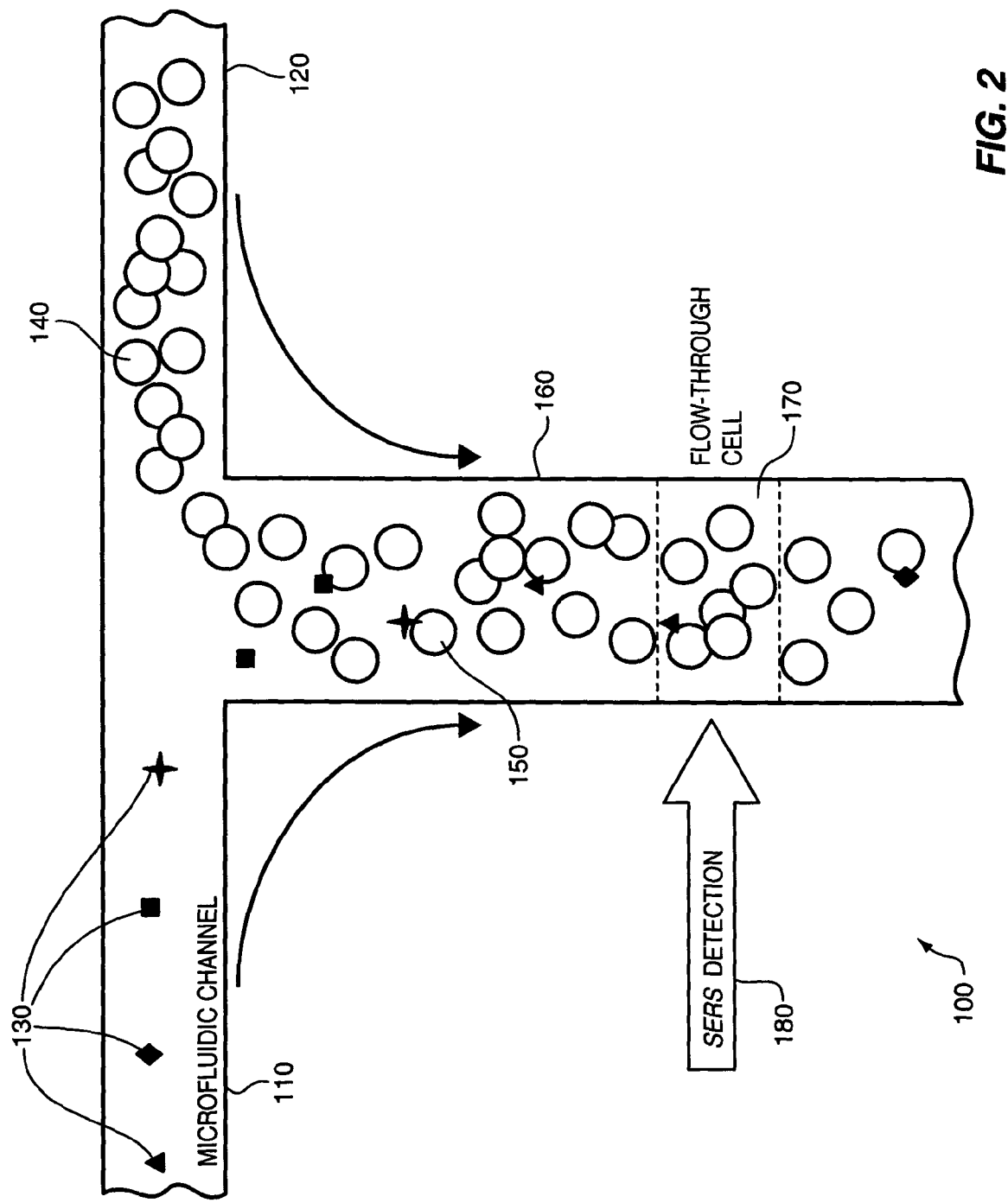
FIG. 2 illustrates an exemplary apparatus 100 (not to scale) and method for nucleic acid 13 sequencing in which the released nucleotides 130 are covalently attached to nanoparticles 140 prior to detection by surface enhanced Raman spectroscopy (SERS) 180.

Another exemplary embodiment of the invention is disclosed in FIG. 2. Nucleotides 130 are released from a nucleic acid by exonuclease activity as discussed above. In certain embodiments of the invention, the nucleotides 130 are unlabeled. Unlabeled nucleic acids directly purified from any organ, tissue and/or cell sample or obtained by known cloning methods may be sequenced using exonuclease treatment. Released nucleotides 130 travel down a microfluidic channel 110.

The released nucleotides 130 are mixed with silver nanoparticles 140, prepared according to Lee and Meisel (*J. Phys. Chem.* 86:3391–3395, 1982). The nanoparticles are 5 to 200 nm in size. Prior to exposure to nucleotides 130, surface-modified nanoparticles 140 are coated with a silane, such as 3-glycidoxypropyltrimethoxysilane (GOP), a reactive linker compound. GOP contains a terminal highly reactive epoxide group. The silanized nanoparticles 140 are mixed with nucleotides 130 and allowed to form covalent cross-links with the nucleotides 130. The nucleotide-nanoparticle complexes 150 pass through a flow through cell 170 and are identified by SERS, SERRS and/or CARS using a Raman detection unit 180. Because of the close proximity of the nucleotides 130 to the nanoparticles 140, the Raman signals are greatly enhanced, allowing detection of single nucleotides 130 passing through the flow-through cell 170.

Example 7

Apparatus for Nucleic Acid Sequencing

Figure 3:
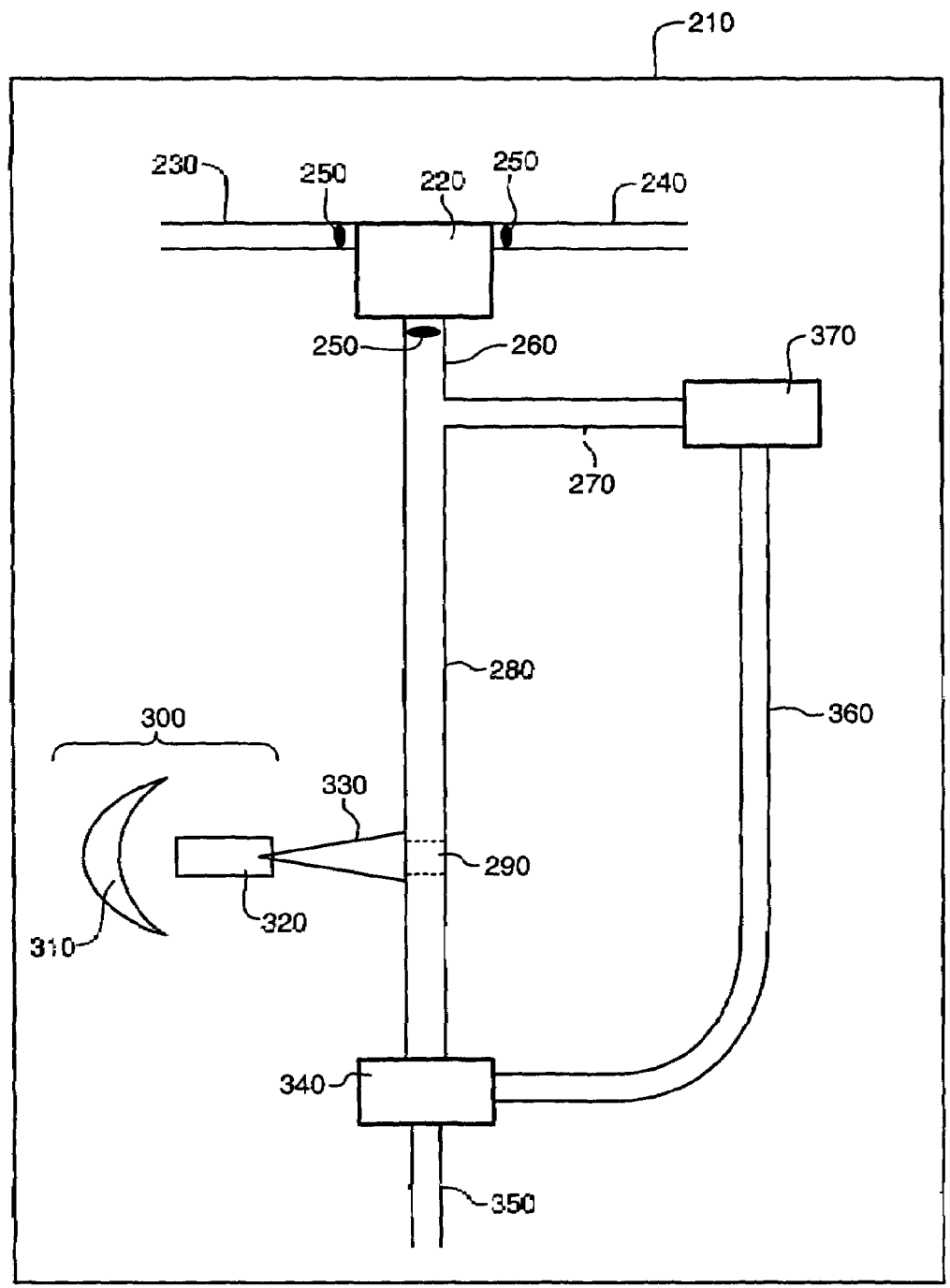
FIG. 3 illustrates another exemplary apparatus 210 (not to scale) for nucleic acid 13 sequencing.

FIG. 3 shows another exemplary embodiment of the invention. A DNA sequencing apparatus 210 comprises a reaction chamber 220 in fluid communication with an influx channel 230 and an efflux channel 240. Fluid movement may be controlled through the use of one or more valves 250. A microfluidic channel 260 is also in fluid communication with the reaction chamber 220. Nucleotides released from one or more nucleic acids by exonuclease activity exit the reaction chamber 220 through the microfluidic channel 260. The nucleotides are mixed with nanoparticles that move through a nanoparticle channel 270 in fluid communication with the microfluidic channel 260. Covalent attachment of nucleotides to nanoparticles occurs within an attachment channel 280. The covalently bound nucleotide-nanoparticle complexes pass through a flow-through cell 290 where the nucleotides are identified by a Raman detection unit 300. The detection unit 300 comprises a laser 320 and Raman detector 310. The laser emits an excitation beam 330 that excites nucleotides within the flow-through cell 290. Excited nucleotides emit a Raman signal that is detected by the Raman detector 310.

In certain embodiments of the invention, nanoparticles may be recovered in a recycling chamber 340. The nanoparticles are chemically treated, for example with acid solutions, and then washed to remove bound nucleotides, linker compounds and any other attached or adsorbed molecules. The nanoparticles may be recycled to a nanoparticle reservoir 370 via a recycling channel 360. In some embodiments of the invention, nanoparticles may be coated with a linker compound, such as GOP, in the recycling channel 360 and/or the nanoparticle reservoir 370. Waste effluent is removed from the recycling chamber 340 via a waste channel 350.

All of the METHODS and APPARATUS disclosed and claimed herein can be made and executed without undue experimentation in light of the present disclosure. It will be apparent to those of skill in the art that variations may be applied to the METHODS and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A method comprising:
   a) obtaining nucleotides covalently linked to gold or silver, or gold or silver nanoparticle(s), wherein the nucleotide and nanoparticles are linked via a terminal reactive cross-linking group, selected from the group consisting of epoxide groups, azido groups, triazine groups, arylazido groups and diazo groups;
   b) synthesizing one or more nucleic acid molecules comprising the gold or silver, or gold or silver nanoparticles;
   c) immobilizing the nucleic acid molecule of step (b) on a solid substrate;
   d) sequentially releasing nucleotides from one end of one or more nucleic acid molecules via an exonuclease;
   e) identifying the released unlabeled nucleotides in a buffer comprising an alkali-metal halide salt by Raman spectroscopy; and
   f) determining the sequence of the nucleic acid molecule.

2. The method of claim 1, wherein single molecules of nucleotides are identified by Raman spectroscopy.

3. The method of claim 2, wherein a single nucleic acid molecule is sequenced.

4. The method of claim 1, wherein multiple nucleic acid molecules of the same sequence or multiple nucleic acid molecules of different sequences are sequenced simultaneously.

5. The method of claim 1, wherein the alkali-metal halide salt is selected from the group consisting of MgCl, CaCl. NaF, KBr, LiI, and LiCl.

6. The method of claim 5, wherein the alkali-metal halide salt is LiCl.

7. The method of claim 1, wherein the linker compound is 3-glycidoxypropyltrimethoxysilane(GOP).

8. The method of claim 1, wherein the released nucleotides are identified by surface enhanced Raman spectroscopy (SERS), surface enhanced resonance Raman spectroscopy (SERRS) and/or coherent anti-Stokes Raman spectroscopy (CARS).

9. The method of claim 1, further comprising separating the nucleotides from the one or more nucleic acid molecules by transferring the released nucleotides through a microfluidic channel.

10. The method of claim 9, wherein microfluidic channel is a metal coated channel.

11. The method of claim 10, wherein the metal is silver, gold, platinum, copper, or aluminum.

12. The method of claim 11, wherein the nanoparticle and microfluidic channel comprise silver.

* * * * *

UNITED STATES PATENT AND TRADEMARK OFFICE
CERTIFICATE OF CORRECTION

PATENT NO. : 7,238,477 B2  Page 1 of 1
APPLICATION NO. : 10/660902
DATED : July 3, 2007
INVENTOR(S) : Xing Su et al.

It is certified that error appears in the above-identified patent and that said Letters Patent is hereby corrected as shown below:

Col. 24 line 53 in Claim 1, Line 15, after the word "released", delete "unlabeled"

Signed and Sealed this

Twenty-fourth Day of June, 2008

JON W. DUDAS
*Director of the United States Patent and Trademark Office*